(12) United States Patent
Grant et al.

(10) Patent No.: US 10,676,522 B2
(45) Date of Patent: Jun. 9, 2020

(54) METHODS OF SELECTIVELY TREATING ASTHMA USING IL-17 ANTAGONISTS

(71) Applicant: Novartis AG, Basel (CH)

(72) Inventors: Sarah Schmidt Grant, Jamaica Plain, MA (US); Shamsah Kazani, Watertown, MA (US); Edward Khokhlovich, Newton, MA (US); Jason Laramie, Westwood, MA (US); Robert Martin Strieter, Falmouth, MA (US); Tricia Ann Thornton-Wells, Lincoln, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/969,952

(22) Filed: May 3, 2018

(65) Prior Publication Data

US 2018/0319881 A1    Nov. 8, 2018

Related U.S. Application Data

(60) Provisional application No. 62/501,806, filed on May 5, 2017.

(51) Int. Cl.
| | |
|---|---|
| *C07K 16/24* | (2006.01) |
| *A61K 39/395* | (2006.01) |
| *G01N 33/68* | (2006.01) |
| *A61P 11/06* | (2006.01) |
| *G01N 33/53* | (2006.01) |
| *A61K 39/00* | (2006.01) |

(52) U.S. Cl.
CPC ........ *C07K 16/244* (2013.01); *A61K 39/3955* (2013.01); *A61P 11/06* (2018.01); *G01N 33/53* (2013.01); *G01N 33/6854* (2013.01); *A61K 2039/505* (2013.01); *C07K 2317/21* (2013.01); *C07K 2317/56* (2013.01); *C07K 2317/565* (2013.01); *C07K 2317/76* (2013.01); *G01N 2800/122* (2013.01); *G01N 2800/52* (2013.01)

(58) Field of Classification Search
None
See application file for complete search history.

(56) References Cited

FOREIGN PATENT DOCUMENTS

WO    2009/124090 A1    10/2009

OTHER PUBLICATIONS

Clinical Trialss .gov; NCT01478360; (CAIN457D2204; 2015).*
Newcomb et al, (Current Opinion in Immunology; 2013, vol. 25, pp. 755-760.*
Rickel, The Journal of Immunology, 2009, 182, 97.9.*
Song et al, Cellular Signaling, 2013, vol. 25, pp. 2335-2347.*
Busse et al, American Journal of Respiratory and Critical Care Medicine 2013; vol. 188, pp. 1294-1302.*
Lu et al, African Journal of Pharmacy and Pharmacology; 2012; vol. 6, No. 40; pp. 2828-2831.*
Paul, Fundamental Immunology, 3rd Edition, 1993, pp. 292-295.*
Casset et al Biochemical and Biophysical Research Communications, 2003; 307:198-205.*
Clinical Trials.gov; Study to Assess the Efficacy and Safety of CJM112 in Patients with Inadequate Controlled Severe Asthma; NIH U.S. National Library of Medicine; Identifier: NCT03299686; Last Posted Jan. 23, 2019; https://clinicaltrials.gov/ct2/show/NCT03299686, p. 1-6.

* cited by examiner

*Primary Examiner* — Bridget E Bunner
*Assistant Examiner* — Fozia Hamud
(74) *Attorney, Agent, or Firm* — Leslie Fischer

(57) ABSTRACT

The disclosure relates to methods, treatment regimens, uses, kits and therapies for treating asthma, such as severe asthma, by employing IL-17 antagonists to a patient population defined by serum concentration of IgE and optionally also an eosinophil count in peripheral blood.

15 Claims, 2 Drawing Sheets
Specification includes a Sequence Listing.

METHODS OF SELECTIVELY TREATING ASTHMA USING IL-17 ANTAGONISTS

TECHNICAL FIELD

The disclosure relates to methods, treatment regimens, uses, kits and therapies for treating asthma, such as moderate to severe asthma, by employing IL-17 antagonists to a patient population defined by serum concentration of IgE below a certain threshold.

BACKGROUND OF THE DISCLOSURE

Asthma is a heterogeneous inflammatory disease of the airways that clinically manifests with symptoms and signs of airflow obstruction of varied severity. Although the majority of asthma patients can be effectively treated with currently available medications, such as inhaled glucocorticoids and bronchodilators, a substantial subset exists who remain difficult-to-treat and manifest with severe disease. These patients account for a relatively large proportion of resource expenditure (Chung et al. 2014).

While asthma has been considered to be driven by T helper cell type 2 (Th2) cells, such as IgE activated mast cells, eosinophils and their products, data suggest that a Th2-high gene signature is present in the airways of only 50% of asthmatics (Woodruff et al. 2009). Non-eosinophilic airway inflammation occurs in approximately 50% of patients with asthma, of which a significant proportion include moderate and severe asthmatics (Thomson 2016). Non-Th2-high or non-eosinophilic inflammation is associated with an impaired therapeutic response to inhaled corticosteroids (McGrath et al. 2012), and hence asthmatics with non-allergic and non-eosinophilic phenotype are not eligible for biologic therapies with anti-IgE and anti-IL5 antibodies. Thus, a large unmet medical need exists in moderate and severe non-allergic non-eosinophilic asthmatics who suffer from symptoms of poorly controlled asthma, such as cough and shortness of breath, despite being compliant on therapy with inhaled glucocorticoids and bronchodilators.

SUMMARY OF THE DISCLOSURE

Increased levels of IL-17A that correlate with the severity of asthma have been reported in the circulation and airways of individuals with asthma compared to healthy controls. High IL-17A mRNA levels have been found in patients with moderate-to-severe asthma, even if those patients were treated with corticosteroids (Bullens et al. 2006). Pre-clinical studies in mouse models of allergic pulmonary inflammation have implicated a requirement for IL-17A and its receptor (IL-17RA) in neutrophilic airway inflammation and steroid-resistant airway hyper-responsiveness. Thus, the properties of IL-17A in vitro, its presence in increased amounts in asthma, and the pre-clinical models of the disease support a role for IL-17A in neutrophilic and/or Th2-low forms of the disease that are poorly responsive to steroids (Cosmi et al. 2011).

However, it also has been shown that an IL-17 pathway antagonizing therapy is not effective in a broad unstratified population of asthma patients (Busse et al., 2013). Furthermore, no patient features have been proven to be conclusively predictive of response to IL-17 antagonizing therapy. The present invention is based on the surprising observation that patients with asthma, such as moderate to severe asthma, having a relatively low level of IgE in serum are more likely to respond to treatment with an IL-17 antagonist.

Thus, according to a first aspect of the present invention, a method of selectively treating a patient having asthma with an IL-17 antagonist is provided, comprising a first step of selecting the patient for treatment with IL-17 antagonist on the basis of the patient having a total serum concentration of IgE below a threshold of 300, 250, 200,150, or 100 international units per milliliter (IU/mL), preferably below 300 IU/mL and most preferably below a threshold of 150 IU/mL, and thereafter, a second step of administering a therapeutically effective amount of IL-17 antagonist to the patient.

In an embodiment, the first step of selecting the patient for treatment with IL-17 antagonist on the basis of the patient also having an eosinophil count in peripheral blood below 300 per µL.

According to a second aspect, a method of selectively treating a patient having asthma is provided, comprising a first step of assaying a biological sample from the patient for a total serum concentration of IgE below a threshold of 300, 250, 200,150, or 100 IU/mL, preferably below 300 IU/mL, and most preferably below a threshold of 150 IU/mL; and thereafter, selectively administering to the patient either: i) a therapeutically effective amount of an IL-17 antagonist on the basis of the biological sample from the patient having a total serum concentration of IgE below a threshold of 300, 250, 200,150, or 100 IU/mL, preferably below 300 IU/mL and most preferably below a threshold of 150 IU/mL; or ii) a therapeutically effective amount of an asthma agent other than an IL-17 antagonist (e.g. a standard-of-care asthma treatment) on the basis of the biological sample from the patient having a total serum concentration of IgE equal to or above the threshold IU/mL.

In an embodiment, the first step also comprises assaying a biologic sample from the patient for eosinophil count in peripheral blood below 300 per µL, and administering an IL-17 antagonist to the patient on the basis of the biological sample from the patient having a total serum concentration of IgE below a threshold of 300 IU/mL and also an eosinophil count in peripheral blood below 300 per µL.

The drug other than an IL-17 antagonist can be any other biologic pharmaceutical used in treatment of asthma, such as omalizumab, mepolizumab, reslizumab or dupilumab.

According to a third aspect, a method of selectively treating a patient having asthma with IL-17 antagonist is provided, comprising a first step of assaying a biological sample from the patient for a total serum concentration of IgE below a threshold of 300, 250, 200,150, or 100 IU/mL, preferably below 300 IU/mL, and most preferably below a threshold of 150 IU/mL; thereafter, selecting the patient for treatment with the IL-17 antagonist on the basis of the biological sample from the patient having a total serum concentration of IgE below a threshold of 150 IU/mL; and thereafter, administering a therapeutically effective amount of the IL-17 antagonist to the patient.

In an embodiment, of the first step also comprises assaying a biologic sample from the patient for eosinophil count in peripheral blood below 300 per µL, and administering an IL-17 antagonist to the patient on the basis of the biological sample from the patient having a total serum concentration of IgE below a threshold of 300 IU/mL and also an eosinophil count in peripheral blood below 300 per µL.

In a preferred embodiment of the first, second or third aspects, the asthma is moderate to severe asthma, such as defined by patients requiring Step 4 therapy as per the Global Strategy for Asthma Management and Prevention's Global Initiative for Asthma, published by the Global Initiative for Asthma (GINA) 2015.

In an embodiment, the step of assaying comprises assaying the biological sample using an immunoassay, such as a sandwich immunoassay.

In another specific embodiment, the step of assaying utilizes the Niji™ total IgE test.

In an embodiment, the biological sample is selected from the group consisting of blood, serum, or plasma, preferably serum.

According to a fourth aspect, a method of selectively treating an asthma patient is provided, comprising administering to the patient an IL-17 antagonist on the basis of the patient having been previously determined to have a total serum concentration of IgE below a threshold of 300 IU/mL.

According to a fifth aspect, an IL-17 antagonist for use in treatment of a patient having asthma is provided, said patient having a total serum concentration of IgE below a threshold of 300, 250, 200,150, or 100 international units per milliliter (IU/mL), preferably below 300 IU/mL, and most preferably below a threshold of 150 IU/mL.

According to a sixth aspect, an IL-17 antagonist for use in treatment of a patient having asthma is provided, the patient is selected by assaying a biological sample from the patient for a total serum concentration of IgE; and selecting the patient on the basis of the biological sample from the patient having a total serum concentration of IgE below a threshold of 300, 250, 200,150, or 100 IU/mL, preferably below 300 IU/mL, and most preferably below a threshold of 150 IU/mL, and optionally an eosinophil count in peripheral blood below 300 per µL.

In an embodiment the IL-17 antagonist for use in treatment of asthma according to the fifth aspect, wherein the patient is selected also by assaying a biological sample from the patient for an eosinophil count in peripheral blood below 300 per µL and selecting the patient on the basis of the biological sample from the patient having a total serum concentration of IgE below a threshold of 300 IU/mL and an eosinophil count in peripheral blood below 300 per µL.

According to a seventh aspect, a method of predicting the likelihood that a patient having asthma will respond to treatment with an IL-17 antagonist, comprising assaying a biological sample from the patient for total serum concentration of IgE, wherein a level of total serum concentration of IgE below a threshold of 300, 250, 200,150, or 100 IU/mL, preferably below 300 IU/mL, and most preferably below a threshold of 150 IU/mL, and optionally also an eosinophil count in peripheral blood below 300 per µL, is indicative of an increased likelihood that the patient will respond to treatment with IL-17 antagonist; and a level of total serum concentration of IgE equal to or above the threshold and optionally also an eosinophil count in peripheral blood below 300 per µL, is indicative of a decreased likelihood that the patient will respond to treatment with IL-17 antagonist.

In an embodiment, the step of assaying comprises assaying the biological sample using an immunoassay, such as a sandwich immunoassay.

In another specific embodiment, the step of assaying utilizes an immunoassay, such as the Niji™ total IgE test.

In an embodiment, the biological sample is selected from the group consisting of blood, serum, or plasma, preferably serum.

According to a eight aspect, a method for producing a transmittable form of information for predicting the responsiveness of a patient having asthma to treatment with IL-17 antagonist is provided, comprising determining an increased likelihood of the patient responding to treatment with the IL-17 antagonist based on the total serum concentration of IgE being below a threshold of 300, 250, 200,150, or 100 IU/mL, preferably below 300 IU/mL and most preferably below a threshold of 150 IU/mL, and optionally also an eosinophil count in peripheral blood below 300 per µL; and recording the result of the determining step on a tangible or intangible media form for use in transmission.

According to an ninth aspect, a kit for use in predicting the likelihood that a patient having asthma will respond to treatment with an IL-17 antagonist is provided, comprising, at least one probe capable of detecting the presence of IgE; and instructions for using the probe to assay a biological sample from the asthma patient for the serum concentration of IgE, wherein a serum concentration of IgE below a threshold of 300, 250, 200,150, or 100 IU/mL, preferably below 300 IU/mL, and most preferably below a threshold of 150 IU/mL, and optionally also an eosinophil count in peripheral blood below 300 per µL is indicative of an increased likelihood that the patient will respond to treatment with the IL-17 antagonist and a serum concentration of IgE equal to or above the threshold, and optionally also an eosinophil count in peripheral blood below 300 per µL is indicative of a decreased likelihood that the patient will respond to treatment with the IL-17 antagonist.

According to a tenth aspect, a kit for use in treating a patient having asthma is provided, comprising, a therapeutically effective amount of an IL-17 antagonist; at least one probe capable of detecting the presence of IgE; instructions for using the probe to assay the serum concentration of IgE in a biological sample from the patient, instructions for administering the IL-17 antagonist to the patient if the biological sample from the patient has a serum concentration of IgE below a threshold of 300, 250, 200,150, or 100 IU/mL, preferably below 300 IU/mL and most preferably below a threshold of 150 IU/mL, and optionally also an eosinophil count in peripheral blood below 300 per µL; and optionally, means for administering the IL-17 antagonist to the patient.

In an embodiment, the probe is a labeled antibody. The label may be selected from a group consisting of a dye molecule, a gold particle, a colored-polymer particle, a fluorescent molecule, an enzyme, a red blood cell, a hemoglobin molecule, a magnetic particle and a carbon particle. In a preferred embodiment, the antibody is specific for IgE and the label is a carbon particle.

In an embodiment, the IL-17 antagonist is an IL-17 binding molecule or an IL-17 receptor binding molecule.

In an embodiment, the IL-17 binding molecule or an IL-17 receptor binding molecule is an IL-17 binding molecule.

In an embodiment, the IL-17 binding molecule is an IL-17 antibody or antigen-binding portion thereof.

(1) In a preferred embodiment the IL-17 antibody or antigen-binding portion thereof is an IL-17 antibody comprising:

an immunoglobulin heavy chain variable domain (VH) comprising the amino acid sequence set forth as SEQ ID NO:30;

an immunoglobulin light chain variable domain (VL) comprising the amino acid sequence set forth as SEQ ID NO:22;

an immunoglobulin VH domain comprising the amino acid sequence set forth as SEQ ID NO:30 and an immunoglobulin VL domain comprising the amino acid sequence set forth as SEQ ID NO:22;

an immunoglobulin VH domain comprising the hypervariable regions set forth as SEQ ID NO:24, SEQ ID NO:26, and SEQ ID NO:28;

an immunoglobulin VL domain comprising the hypervariable regions set forth as SEQ ID NO:16, SEQ ID NO:18 and SEQ ID NO:20;

an immunoglobulin VH domain comprising the hypervariable regions set forth as SEQ ID NO:25, SEQ ID NO:27 and SEQ ID NO:29;

an immunoglobulin VL domain comprising the hypervariable regions set forth as SEQ ID NO:17, SEQ ID NO:19 and SEQ ID NO:21;

an immunoglobulin VH domain comprising the hypervariable regions set forth as SEQ ID NO:24, SEQ ID NO:26, and SEQ ID NO:28 and an immunoglobulin VL domain comprising the hypervariable regions set forth as SEQ ID NO:16, SEQ ID NO:18 and SEQ ID NO:20; and an immunoglobulin VH domain comprising the hypervariable regions set forth as SEQ ID NO:25, SEQ ID NO:27 and SEQ ID NO:29 and an immunoglobulin VL domain comprising the hypervariable regions set forth as SEQ ID NO:17, SEQ ID NO:19 and SEQ ID NO:21.

(2) In a particularly preferred embodiment, the human IL-17 antibody comprises the light chain set forth as SEQ ID NO:23 and the heavy chain set forth as SEQ ID NO:31.

(3) In yet another preferred embodiment of the disclosed uses, methods and kits, the IL-17 antibody or antigen-binding fragment comprises: i) an immunoglobulin heavy chain variable domain (VH) comprising the amino acid sequence set forth as SEQ ID NO:8; ii) an immunoglobulin light chain variable domain (VL) comprising the amino acid sequence set forth as SEQ ID NO:10; iii) an immunoglobulin VH domain comprising the amino acid sequence set forth as SEQ ID NO:8 and an immunoglobulin VL domain comprising the amino acid sequence set forth as SEQ ID NO:10; iv) an immunoglobulin VH domain comprising the hypervariable regions set forth as SEQ ID NO:1, SEQ ID NO:2, and SEQ ID NO:3; v) an immunoglobulin VL domain comprising the hypervariable regions set forth as SEQ ID NO:4, SEQ ID NO:5 and SEQ ID NO:6; vi) an immunoglobulin VH domain comprising the hypervariable regions set forth as SEQ ID NO:11, SEQ ID NO:12 and SEQ ID NO:13; vii) an immunoglobulin VH domain comprising the hypervariable regions set forth as SEQ ID NO:1, SEQ ID NO:2, and SEQ ID NO:3 and an immunoglobulin VL domain comprising the hypervariable regions set forth as SEQ ID NO:4, SEQ ID NO:5 and SEQ ID NO:6; viii) an immunoglobulin VH domain comprising the hypervariable regions set forth as SEQ ID NO:11, SEQ ID NO:12 and SEQ ID NO:13 and an immunoglobulin VL domain comprising the hypervariable regions set forth as SEQ ID NO:4, SEQ ID NO:5 and SEQ ID NO:6; ix) an immunoglobulin light chain comprising the amino acid sequence set forth as SEQ ID NO:14; x) an immunoglobulin heavy chain comprising the amino acid sequence set forth as SEQ ID NO:15; or xi) an immunoglobulin light chain comprising the amino acid sequence set forth as SEQ ID NO:14 and an immunoglobulin heavy chain comprising the amino acid sequence set forth as SEQ ID NO:15.

(4) In a particularly preferred embodiment, the IL-17 antibody comprises the light chain set forth as SEQ ID NO:14 and the heavy chain set forth as SEQ ID NO:15.

The IL-17 antibody may be a human antibody, preferably a monoclonal human antibody.

Additional methods, uses, and kits are provided in the following description and appended claims. Further features, advantages and aspects of the present disclosure will become apparent to those skilled in the art from the following description and appended claims.

DETAILED DESCRIPTION OF THE DISCLOSURE

Figure 1:
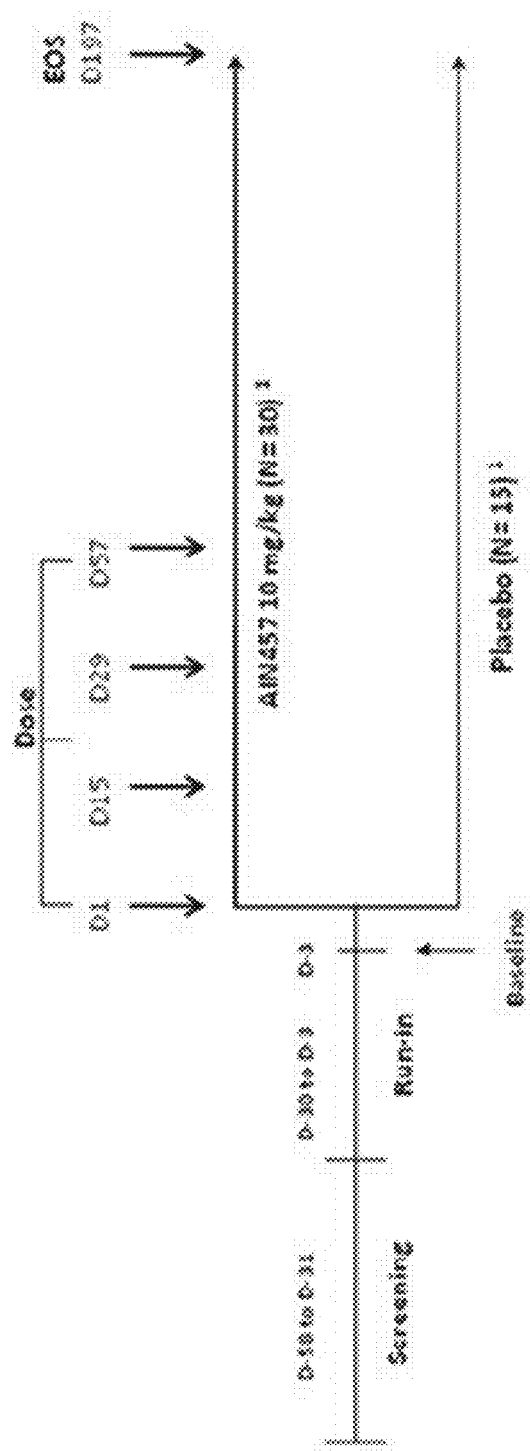
FIG. 1 is a schematic representation of a study design.

The aim of this disclosure is to provide a therapy with anti-IL17 antibodies for addressing the unmet medical need in patients with asthma, such as moderate and severe asthma.

Specific embodiments of the invention will be elucidated in the following detailed description.

Definitions

The term "comprising" encompasses "including" as well as "consisting," e.g., a composition "comprising" X may consist exclusively of X or may include something additional, e.g., X+Y.

The term "assaying" is used to refer to the act of identifying, screening, probing, testing measuring or determining, which act may be performed by any conventional means. For example, a sample may be assayed for the presence of a particular genetic or protein marker by using an ELISA assay, a Northern blot, imaging, serotyping, cellular typing, gene sequencing, phenotyping, haplotyping, immunohistochemistry, western blot, mass spectrometry, etc. The term "detecting" (and the like) means the act of extracting particular information from a given source. The terms "assaying" and "determining" contemplate a transformation of matter, e.g., a transformation of a biological sample, e.g., a blood sample or other tissue sample, from one state to another by means of subjecting that sample to physical testing.

The term "obtaining" means to procure, e.g., to acquire possession of in any way, e.g., by physical intervention (e.g., biopsy, blood draw) or non-physical intervention (e.g, transmittal of information via a server), etc.

The phrase "assaying a biological sample . . . " and the like is used to mean that a sample may be tested (either directly or indirectly) for concentration of IgE.

The term "about" in relation to a numerical value x means, for example, +/−10%. When used in front of a numerical range or list of numbers, the term "about" applies to each number in the series, e.g., the phrase "about 1-5" should be interpreted as "about 1-about 5", or, e.g., the phrase "about 1, 2, 3, 4" should be interpreted as "about 1, about 2, about 3, about 4, etc."

The word "substantially" does not exclude "completely," e.g., a composition which is "substantially free" from Y may be completely free from Y. Where necessary, the word "substantially" may be omitted from the definition of the disclosure.

The term "antibody" as referred to herein includes naturally-occurring and whole antibodies. A naturally-occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL.

The V$_H$ and V$_L$ regions can be further subdivided into regions of hypervariability, termed hypervariable regions or complementarity determining regions (CDR), interspersed with regions that are more conserved, termed framework regions (FR). Each V$_H$ and V$_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. Exemplary antibodies include secukinumab (Table 1), CJM112 (Table 2) and ixekizumab (U.S. Pat. No. 7,838,638, which is incorporated by reference in its entirety).

The term "antigen-binding fragment" of an antibody, as used herein, refers to fragments of an antibody that retain the ability to specifically bind to an antigen (e.g., IL-17). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the V$_L$, V$_H$, CL and CH1 domains; a F(ab)2 fragment, a bivalent fragment comprising two Fab fragments linked by a disulfide bridge at the hinge region; a Fd fragment consisting of the V$_H$ and CH1 domains; a Fv fragment consisting of the V$_L$ and V$_H$ domains of a single arm of an antibody; a dAb fragment (Ward et al., 1989 Nature 341:544-546), which consists of a V$_H$ domain; and an isolated CDR. Exemplary antigen-binding sites include the CDRs of secukinumab (AIN457) as set forth in SEQ ID NOs: 1-6 and 11-13 (Table 1), preferably the heavy chain CDR3. Exemplary antigen-binding sites include the CDRs of CJM112 as set forth in SEQ ID NOs: 16-21 and 24-29 (Table 2), preferably the heavy chain CDR3. Furthermore, although the two domains of the Fv fragment, V$_L$ and V$_H$, are coded for by separate genes, they can be joined, using recombinant methods, by a synthetic linker that enables them to be made as a single protein chain in which the V$_L$ and V$_H$ regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies are also intended to be encompassed within the term "antibody". Single chain antibodies and antigen-binding portions are obtained using conventional techniques known to those of skill in the art.

An "isolated antibody", as used herein, refers to an antibody that is substantially free of other antibodies having different antigenic specificities (e.g., an isolated antibody that specifically binds IL-17 is substantially free of antibodies that specifically bind antigens other than IL-17). The term "monoclonal antibody" or "monoclonal antibody composition" as used herein refer to a preparation of antibody molecules of single molecular composition. The term "human antibody", as used herein, is intended to include antibodies having variable regions in which both the framework and CDR regions are derived from sequences of human origin. A "human antibody" need not be produced by a human, human tissue or human cell. The human antibodies of the disclosure may include amino acid residues not encoded by human sequences (e.g., mutations introduced by random or site-specific mutagenesis in vitro, by N-nucleotide addition at junctions in vivo during recombination of antibody genes, or by somatic mutation in vivo). In some embodiments of the disclosed processes and compositions, the IL-17 antibody is a human antibody, an isolated antibody, and/or a monoclonal antibody.

The term "IL-17" refers to interleukin 17A, IL-17A, formerly known as CTLA8, and includes wild-type IL-17A from various species (e.g., human, mouse, and monkey), polymorphic variants of IL-17A, and functional equivalents of IL-17A. Functional equivalents of IL-17A according to the present disclosure preferably have at least about 65%, 75%, 85%, 95%, 96%, 97%, 98%, or even 99% overall sequence identity with a wild-type IL-17A (e.g., human IL-17A), and substantially retain the ability to induce IL-6 production by human dermal fibroblasts.

"IL-17 antagonist" as used herein refers to a molecule capable of antagonizing (e.g., reducing, inhibiting, decreasing, delaying) IL-17 function, expression and/or signalling (e.g., by blocking the binding of IL-17 to the IL-17 receptor). Non-limiting examples of IL-17 antagonists include IL-17 binding molecules and IL-17 receptor binding molecules. In some embodiments of the disclosed methods, regimens, kits, processes, uses and compositions, an IL-17 antagonist is employed.

By "IL-17 binding molecule" is meant any molecule capable of binding to the human IL-17 antigen either alone or associated with other molecules. The binding reaction may be shown by qualitative assays including, for example, a binding assay, competition assay or a bioassay for determining the inhibition of IL-17 binding to its receptor or any kind of binding assays, with reference to a negative control test in which an antibody of unrelated specificity, but ideally of the same isotype, e.g., an anti-CD25 antibody, is used. Non-limiting examples of IL-17 binding molecules include small molecules, IL-17 receptor decoys, and antibodies that bind to IL-17 as produced by B-cells or hybridomas and chimeric, CDR-grafted or human antibodies or any fragment thereof, e.g., F(ab')$_2$ and Fab fragments, as well as single chain or single domain antibodies. Preferably the IL-17 binding molecule antagonizes (e.g., reduces, inhibits, decreases, delays) IL-17 function, expression and/or signaling. In some embodiments of the disclosed methods, regimens, kits, processes, uses and compositions, an IL-17 binding molecule is employed.

By "IL-17 receptor binding molecule" is meant any molecule capable of binding to the human IL-17 receptor either alone or associated with other molecules. The binding reaction may be shown by standard methods (qualitative assays) including, for example, a binding assay, competition assay or a bioassay for determining the inhibition of IL-17 receptor binding to IL-17 or any kind of binding assays, with reference to a negative control test in which an antibody of unrelated specificity, but ideally of the same isotype, e.g., an anti-CD25 antibody, is used. Non-limiting examples of IL-17 receptor binding molecules include small molecules, IL-17 decoys, and antibodies to the IL-17 receptor as produced by B-cells or hybridomas and chimeric, CDR-grafted or human antibodies or any fragment thereof, e.g., F(ab')$_2$ and Fab fragments, as well as single chain or single domain antibodies. One such IL-17 receptor antibody is brodalumab (AMG827), as disclosed in U.S. Pat. No. 7,767,206, which is incorporated by reference in its entirety. Preferably the IL-17 receptor binding molecule antagonizes (e.g., reduces, inhibits, decreases, delays) IL-17 function, expression and/or signaling. In some embodiments of the disclosed methods, regimens, kits, processes, uses and compositions, an IL-17 receptor binding molecule is employed, preferably brodalumab.

The term IgE refers to immunoglobulin E, well known to a person skilled in the art.

IgE is measured in international units per milliliter (IU/mL) as disclosed, e.g., in Seagroatt and Anderson (1981).

An eosinophil count is a blood test that measures the number of white blood cells called eosinophils. Blood is drawn from a vein, typically on the inside of the elbow or the back of the hand or using a tool such as a lancet to prick the skin. The blood is put in a small glass tube, or onto a slide or test strip. In a lab, the blood is placed on a microscope slide, and a stain is added to the sample. This causes eosinophils to show up as orange-red granules which make it possible to count how many eosinophils are present in a specific volume of blood, such as one microliter (µL).

The term "$K_D$" is intended to refer to the dissociation rate of a particular antibody-antigen interaction. The term "$K_D$", as used herein, is intended to refer to the dissociation constant, which is obtained from the ratio of $k_{off}$ to $k_{on}$ (i.e., $k_{off}/k_{on}$) and is expressed as a molar concentration (M). $K_D$ values for antibodies can be determined using methods well established in the art. A method for determining the $K_D$ of an antibody is by using surface plasmon resonance, or using a biosensor system such as a Biacore® system. In some embodiments, the IL-17 antibody or antigen-binding fragment thereof, e.g., secukinumab or CJM112, binds human IL-17 with a $K_D$ of about 1-250 pM, preferably about 1-10 pM (e.g., about 6 pM) or about 100-200 pM (e.g., about 200 pM).

The term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. Standard assays to evaluate the binding affinity of the antibodies toward IL-17 of various species are known in the art, including for example, ELISAs, western blots and RIAs. The binding kinetics (e.g., binding affinity) of the antibodies also can be assessed by standard assays known in the art, such as by Biacore analysis.

An antibody that "inhibits" one or more of these IL-17 functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (or when a control antibody of irrelevant specificity is present). An antibody that inhibits IL-17 activity affects a statistically significant decrease, e.g., by at least about 10% of the measured parameter, by at least 50%, 80% or 90%, and in certain embodiments of the disclosed methods and compositions, the IL-17 antibody used may inhibit greater than 95%, 98% or 99% of IL-17 functional activity.

The term "derivative", unless otherwise indicated, is used to define amino acid sequence variants, and covalent modifications (e.g., pegylation, deamidation, hydroxylation, phosphorylation, methylation, etc.) of an IL-17 antibody or antigen-binding fragment thereof, e.g., secukinumab or CJM112, according to the present disclosure, e.g., of a specified sequence (e.g., a variable domain). A "functional derivative" includes a molecule having a qualitative biological activity in common with the disclosed IL-17 antibodies. A functional derivative includes fragments and peptide analogs of an IL-17 antibody as disclosed herein. Fragments comprise regions within the sequence of a polypeptide according to the present disclosure, e.g., of a specified sequence. Functional derivatives of the IL-17 antibodies disclosed herein (e.g., functional derivatives of secukinumab or CJM112) preferably comprise $V_H$ and/or $V_L$ domains that have at least about 65%, 75%, 85%, 95%, 96%, 97%, 98%, or even 99% overall sequence identity with the $V_H$ and/or $V_L$ sequences of the IL-17 antibodies and antigen-binding fragments thereof disclosed herein, and substantially retain the ability to bind human IL-17 or, e.g., inhibit IL-6 production of IL-17 induced human dermal fibroblasts.

The phrase "substantially identical" means that the relevant amino acid or nucleotide sequence (e.g., $V_H$ or $V_L$ domain) will be identical to or have insubstantial differences (e.g., through conserved amino acid substitutions) in comparison to a particular reference sequence. Insubstantial differences include minor amino acid changes, such as 1 or 2 substitutions in a 5 amino acid sequence of a specified region (e.g., $V_H$ or $V_L$ domain). In the case of antibodies, the second antibody has the same specificity and has at least 50% of the affinity of the same. Sequences substantially identical (e.g., at least about 85% sequence identity) to the sequences disclosed herein are also part of this application. In some embodiments, the sequence identity of a derivative IL-17 antibody (e.g., a derivative of secukinumab or CJM112, e.g., a secukinumab or CJM112 biosimilar antibody) can be about 90% or greater, e.g., 90%, 91%, 92%, 93%, 94%, 95%, 96%, 97%, 98%, 99% or higher relative to the disclosed sequences.

"Identity" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent identity, and not considering any conservative substitutions as part of the sequence identity. Neither N- or C-terminal extensions nor insertions shall be construed as reducing identity. Methods and computer programs for the alignment are well known. The percent identity can be determined by standard alignment algorithms, for example, the Basic Local Alignment Search Tool (BLAST) described by Altshul et al. ((1990) J. Mol. Biol., 215: 403 410); the algorithm of Needleman et al. ((1970) J. Mol. Biol., 48: 444 453); or the algorithm of Meyers et al. ((1988) Comput. Appl. Biosci., 4: 11 17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

As used herein, "predicting" indicates that the methods described herein provide information to enable a health care provider to determine the likelihood that an individual having asthma, such as moderate to severe asthma, will respond to or will respond more favorably to treatment with an IL-17 binding molecule. It does not refer to the ability to predict response with 100% accuracy. Instead, the skilled artisan will understand that it refers to an increased probability.

As used herein, "likelihood" and "likely" is a measurement of how probable an event is to occur. It may be used interchangably with "probability". Likelihood refers to a probability that is more than speculation, but less than certainty. Thus, an event is likely if a reasonable person using common sense, training or experience concludes that, given the circumstances, an event is probable. In some embodiments, once likelihood has been ascertained, the patient may be treated (or treatment continued, or treatment proceed with a dosage modification) with the IL-17 binding molecule or the patient may not be treated (or treatment discontinued, or treatment proceed with a dosage modification) with the IL-17 binding molecule.

The phrase "increased likelihood" refers to an increase in the probability that an event will occur. For example, some methods herein allow prediction of whether a patient will display an increased likelihood of responding to treatment with an IL-17 binding molecule or an increased likelihood of responding better to treatment with an IL-17 binding molecule in comparison to an asthma patient with a serum concentration of IgE of 150 IU/mL or above.

"Amino acid(s)" refer to all naturally occurring L-α-amino acids, e.g., and include D-amino acids. The phrase "amino acid sequence variant" refers to molecules with some differences in their amino acid sequences as compared to the sequences according to the present disclosure. Amino acid sequence variants of an antibody according to the present disclosure, e.g., of a specified sequence, still have the ability to bind the human IL-17 or, e.g., inhibit IL-6 production of IL-17 induced human dermal fibroblasts. Amino acid sequence variants include substitutional variants (those that have at least one amino acid residue removed and a different amino acid inserted in its place at the same position in a polypeptide according to the present disclosure), insertional variants (those with one or more amino acids inserted immediately adjacent to an amino acid at a particular position in a polypeptide according to the present disclosure) and deletional variants (those with one or more amino acids removed in a polypeptide according to the present disclosure).

The term "pharmaceutically acceptable" means a non-toxic material that does not interfere with the effectiveness of the biological activity of the active ingredient(s).

The term "administering" in relation to a compound, e.g., an IL-17 binding molecule or another agent, is used to refer to delivery of that compound to a patient by any route.

As used herein, a "therapeutically effective amount" refers to an amount of an IL-17 antagonist, e.g., IL-17 binding molecule (e.g., IL-17 antibody or antigen-binding fragment thereof, e.g., secukinumab or CJM112) or IL-17 receptor binding molecule (e.g., IL-17 antibody or antigen-binding fragment thereof) that is effective, upon single or multiple dose administration to a patient (such as a human) for treating, preventing, preventing the onset of, curing, delaying, reducing the severity of, ameliorating at least one symptom of a disorder or recurring disorder, or prolonging the survival of the patient beyond that expected in the absence of such treatment. When applied to an individual active ingredient (e.g., an IL-17 antagonist, e.g., secukinumab or CJM112) administered alone, the term refers to that ingredient alone. When applied to a combination, the term refers to combined amounts of the active ingredients that result in the therapeutic effect, whether administered in combination, serially or simultaneously.

The term "treatment" or "treat" is herein defined as the application or administration of an IL-17 antibody according to the disclosure, for example, secukinumab or ixekizumab, or a pharmaceutical composition comprising said anti-IL-17 antibody, to a subject or to an isolated tissue or cell line from a subject, where the subject has a particular disease (e.g., psoriasis), a symptom associated with the disease (e.g., psoriasis), or a predisposition towards development of the disease (e.g., psoriasis), where the purpose is to cure (if applicable), delay the onset of, reduce the severity of, alleviate, ameliorate one or more symptoms of the disease, improve the disease, reduce or improve any associated symptoms of the disease or the predisposition toward the development of the disease. The term "treatment" or "treat" includes treating a patient suspected to have the disease as well as patients who are ill or who have been diagnosed as suffering from the disease or medical condition, and includes suppression of clinical relapse. As used herein, "selecting" and "selected" in reference to a patient is used to mean that a particular patient is specifically chosen from a larger group of patients on the basis of (due to) the particular patient having a predetermined criteria. Similarly, "selectively treating" refers to providing treatment to a patient having a particular disease, where that patient is specifically chosen from a larger group of patients on the basis of the particular patient having a predetermined criterion. Similarly, "selectively administering" refers to administering a drug to a patient that is specifically chosen from a larger group of patients on the basis of (due to) the particular patient having a predetermined criterion. By selecting, selectively treating and selectively administering, it is meant that a patient is delivered a personalized therapy based on the patient's personal history (e.g., prior therapeutic interventions, e.g., prior treatment with biologics), biology (e.g., particular genetic markers), and/or manifestation (e.g., not fulfilling particular diagnostic criteria), rather than being delivered a standard treatment regimen based solely on the patient's membership in a larger group. Selecting, in reference to a method of treatment as used herein, does not refer to fortuitous treatment of a patient having a particular criterion, but rather refers to the deliberate choice to administer treatment to a patient based on the patient having a particular criterion. Thus, selective treatment/administration differs from standard treatment/administration, which delivers a particular drug to all patients having a particular disease, regardless of their personal history, manifestations of disease, and/or biology.

As used herein, the phrase "asthma" refers to a common and potentially serious chronic disease of the respiratory tract characterized by airway inflammation and constriction leading to symptoms such as wheezing, shortness of breath, chest tightness and cough that vary over time in their occurrence, frequency, intensity and response to therapy.

The term "moderate to severe asthma" refers to the severity of the intrinsic intensity of the disease. This is described in great detail in the publication Global strategy for asthma management and prevention, issued by Global Initiative for Asthma in 2015. Here, a patient is defined as having moderate to severe asthma if he/she requires treatment recommended at Step 4 and higher in the control-based asthma management cycle (Global strategy for asthma management and prevention, GINA report 2015, page 31).

Asthma severity is assessed retrospectively from the level of treatment required to control symptoms and exacerbations. It can be assessed once the patient has been on controller treatment for several months and, if appropriate, treatment step down has been attempted to find the patient's minimum effective level of treatment. Asthma severity is not a static feature and may change over months or years.

Asthma severity can be assessed when the patient has been on regular controller treatment for several months. Mild asthma is asthma that is well controlled with Step 1 or Step 2 treatment (Box 3-5, p31), i.e. with as-needed reliever medication alone, or with low-intensity controller treatment such as low dose ICS, leukotriene receptor antagonists or chromones. Moderate asthma is asthma that is well controlled with Step 3 treatment e.g. low dose ICS/LABA. Severe asthma is asthma that requires Step 4 or 5 treatment (Box 3-5, p31), e.g., high-dose ICS/LABA, to prevent it from becoming uncontrolled, or asthma that remains uncontrolled despite this treatment. While many patients with uncontrolled asthma may be difficult to treat due to inadequate or inappropriate treatment, or persistent problems with adherence or comorbidities such as chronic rhinosinusitis or obesity, the European Respiratory Society/American Thoracic Society Task Force on Severe Asthma considered that the definition of severe asthma should be reserved for patients with refractory asthma and those in whom response to treatment of comorbidities is incomplete.

"Asthma agent" means any compound useful to treat asthma.

"FEV" refers to forced expiratory volume, and "FEV1" is the maximal volume of air exhaled in the first second of a forced expiration from a position of full inspiration, expressed in liters at body temperature and ambient pressure saturation with water vapor, measured according to Miller M R, et al. (2005) Standardisation of spirometry. Eur. Respir. J. 26:319-338.

IL-17 Antagonists

The various disclosed processes, kits, uses and methods utilize an IL-17 antagonist. IL-17 antagonists include small molecules and biological molecules that are capable of blocking, reducing and/or inhibiting IL-17 signal, activity and/or transduction. Examples of IL-17 antagonists include, e.g., IL-17 binding molecules (e.g., soluble IL-17 receptors, IL-17 antibodies or antigen-binding fragments thereof, e.g., secukinumab or CJM112) and IL-17 receptor binding molecules (e.g., IL-17 receptor antibodies or antigen-binding fragments thereof). In some embodiments, the IL-17 antagonist is an IL-17 binding molecule, preferably an IL-17 antibody or antigen-binding fragment thereof. IL-17 antibodies and antigen-binding fragment thereof as used herein can be fully-human, CDR-grafted, or chimeric. It is preferable that the constant region domains of an antibody or antigen-binding fragment thereof for use in the disclosed methods, uses, kits, etc. preferably comprise suitable human constant region domains, for instance as described in "Sequences of Proteins of Immunological Interest", Kabat E. A. et al, US Department of Health and Human Services, Public Health Service, National Institute of Health.

Particularly preferred IL-17 antibodies or antigen-binding fragments thereof used in the disclosed methods are human antibodies, especially secukinumab as described in Examples 1 and 2 of WO 2006/013107 and CJM112 as described in U.S. Pat. No. 9,193,788, both of which are incorporated by reference herein in their entirety. Secukinumab and CJM112 are recombinant high-affinity, fully human monoclonal anti-human interleukin-17A (IL-17A, IL-17) antibodies of the IgG$_1$/kappa isotype. Secukinumab has a high affinity for IL-17, i.e., a K$_D$ of about 100-200 pM (e.g., about 200 pM), an IC$_{50}$ of about 0.4 nM for in vitro neutralization of the biological activity of about 0.67 nM human IL-17A, and a half-life of about 4 weeks. CJM112 has a very high affinity for human IL-17A, i.e., about 1-10 pM (e.g., about 6 pM), and an in vivo half-life of about 2-4 weeks, e.g., about 3 weeks.

1. Secukinumab

For ease of reference the amino acid sequences of the hypervariable regions of the secukinumab monoclonal antibody, based on the Kabat definition and as determined by the X-ray analysis and using the approach of Chothia and coworkers, is provided in Table 1, below.

TABLE 1

Amino acid sequence identifiers of the hypervariable regions of secukinumab. The DNA encoding the VL of secukinumab is set forth in SEQ ID NO: 9. The DNA encoding the VH of secukinumab is set forth in SEQ ID NO: 7.

| Secukinumab Light-Chain | | |
|---|---|---|
| CDR1' | Kabat | SEQ ID NO: 4 |
|  | Chothia | SEQ ID NO: 4 |
| CDR2' | Kabat | SEQ ID NO: 5 |
|  | Chothia | SEQ ID NO: 5 |
| CDR2' | Kabat | SEQ ID NO: 6 |
|  | Chothia | SEQ ID NO: 6 |
| VL |  | SEQ ID NO: 10 |
| Light Chain |  | SEQ ID NO: 14 |
| Secukinumab Heavy-Chain | | |
| CDR1 | Kabat | SEQ ID NO: 1 |
| CDR1-x | Chothia | SEQ ID NO: 11 |
| CDR2 | Kabat | SEQ ID NO: 2 |
| CDR2-x | Chothia | SEQ ID NO: 12 |
| CDR3 | Kabat | SEQ ID NO: 3 |
| CDR3-x | Chothia | SEQ ID NO: 13 |
| VH |  | SEQ ID NO: 8 |
| Heavy Chain |  | SEQ ID NO: 15 |

In one embodiment, the IL-17 antibody or antigen-binding fragment thereof comprises at least one immunoglobulin heavy chain variable domain (V$_H$) comprising hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3. In one embodiment, the IL-17 antibody or antigen-binding fragment thereof comprises at least one immunoglobulin light chain variable domain (V$_L$') comprising hypervariable regions CDR1', CDR2' and CDR3', said CDR1' having the amino acid sequence SEQ ID NO:4, said CDR2' having the amino acid sequence SEQ ID NO:5 and said CDR3' having the amino acid sequence SEQ ID NO:6. In one embodiment, the IL-17 antibody or antigen-binding fragment thereof comprises at least one immunoglobulin heavy chain variable domain (V$_H$) comprising hypervariable regions CDR1-x, CDR2-x and CDR3-x, said CDR1-x having the amino acid sequence SEQ ID NO:11, said CDR2-x having the amino acid sequence SEQ ID NO:12, and said CDR3-x having the amino acid sequence SEQ ID NO:13.

In one embodiment, the IL-17 antibody or antigen-binding fragment thereof comprises at least one immunoglobulin V$_H$ domain and at least one immunoglobulin V$_L$ domain, wherein: a) the immunoglobulin V$_H$ domain comprises (e.g., in sequence): i) hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3; or ii) hypervariable regions CDR1-x, CDR2-x and CDR3-x, said CDR1-x having the amino acid sequence SEQ ID NO:11, said CDR2-x having the amino acid sequence SEQ ID NO:12, and said CDR3-x having the amino acid sequence SEQ ID NO:13; and b) the immunoglobulin V$_L$ domain comprises (e.g., in sequence) hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6.

In one embodiment, the IL-17 antibody or antigen-binding fragment thereof comprises: a) an immunoglobulin heavy chain variable domain (V$_H$) comprising the amino acid sequence set forth as SEQ ID NO:8; b) an immunoglobulin light chain variable domain (V$_L$) comprising the amino acid sequence set forth as SEQ ID NO:10; c) an immunoglobulin V$_H$ domain comprising the amino acid sequence set forth as SEQ ID NO:8 and an immunoglobulin V$_L$ domain comprising the amino acid sequence set forth as SEQ ID NO:10; d) an immunoglobulin V$_H$ domain comprising the hypervariable regions set forth as SEQ ID NO:1, SEQ ID NO:2, and SEQ ID NO:3; e) an immunoglobulin V$_L$ domain comprising the hypervariable regions set forth as SEQ ID NO:4, SEQ ID NO:5 and SEQ ID NO:6; f) an immunoglobulin V$_H$ domain comprising the hypervariable regions set forth as SEQ ID NO:11, SEQ ID NO:12 and SEQ ID NO:13; g) an immunoglobulin V$_H$ domain comprising the hypervariable regions set forth as SEQ ID NO:1, SEQ ID NO:2, and SEQ ID NO:3 and an immunoglobulin V$_L$ domain comprising the hypervariable regions set forth as SEQ ID NO:4, SEQ ID NO:5 and SEQ ID NO:6; or h) an immunoglobulin V$_H$ domain comprising the hypervariable regions set forth as SEQ ID NO:11, SEQ ID NO:12 and SEQ ID NO:13 and an immunoglobulin V$_L$ domain comprising the hypervariable regions set forth as SEQ ID NO:4, SEQ ID NO:5 and SEQ ID NO:6.

In some embodiments, the IL-17 antibody or antigen-binding fragment thereof (e.g., secukinumab) comprises the three CDRs of SEQ ID NO:10. In other embodiments, the IL-17 antibody or antigen-binding fragment thereof comprises the three CDRs of SEQ ID NO:8. In other embodiments, the IL-17 antibody or antigen-binding fragment thereof comprises the three CDRs of SEQ ID NO:10 and the three CDRs of SEQ ID NO:8. CDRs of SEQ ID NO:8 and SEQ ID NO:10 may be found in Table 1. The free cysteine in the light chain (CysL97) may be seen in SEQ ID NO:6.

In some embodiments, IL-17 antibody or antigen-binding fragment thereof comprises the light chain of SEQ ID NO:14. In other embodiments, the IL-17 antibody or antigen-binding fragment thereof comprises the heavy chain of SEQ ID NO:15. In other embodiments, the IL-17 antibody or antigen-binding fragment thereof comprises the light chain of SEQ ID NO:14 and the heavy domain of SEQ ID NO:15. In some embodiments, the IL-17 antibody or antigen-binding fragment thereof comprises the three CDRs of SEQ ID NO:14. In other embodiments, IL-17 antibody or antigen-binding fragment thereof comprises the three CDRs of SEQ ID NO:15. In other embodiments, the IL-17 antibody or antigen-binding fragment thereof comprises the three CDRs of SEQ ID NO:14 and the three CDRs of SEQ ID NO:15. CDRs of SEQ ID NO:14 and SEQ ID NO:15 may be found in Table 1.

Hypervariable regions may be associated with any kind of framework regions, though preferably are of human origin. Suitable framework regions are described in Kabat E. A. et al, ibid. The preferred heavy chain framework is a human heavy chain framework, for instance that of the secukinumab antibody. It consists in sequence, e.g. of FR1 (amino acid 1 to 30 of SEQ ID NO:8), FR2 (amino acid 36 to 49 of SEQ ID NO:8), FR3 (amino acid 67 to 98 of SEQ ID NO:8) and FR4 (amino acid 117 to 127 of SEQ ID NO:8) regions. Taking into consideration the determined hypervariable regions of secukinumab by X-ray analysis, another preferred heavy chain framework consists in sequence of FR1-x (amino acid 1 to 25 of SEQ ID NO:8), FR2-x (amino acid 36 to 49 of SEQ ID NO:8), FR3-x (amino acid 61 to 95 of SEQ ID NO:8) and FR4 (amino acid 119 to 127 of SEQ ID NO:8) regions. In a similar manner, the light chain framework consists, in sequence, of FR1' (amino acid 1 to 23 of SEQ ID NO:10), FR2' (amino acid 36 to 50 of SEQ ID NO:10), FR3' (amino acid 58 to 89 of SEQ ID NO:10) and FR4' (amino acid 99 to 109 of SEQ ID NO:10) regions.

In one embodiment, the IL-17 antibody or antigen-binding fragment thereof (e.g., secukinumab) is selected from a human IL-17 antibody that comprises at least: a) an immunoglobulin heavy chain or fragment thereof which comprises a variable domain comprising, in sequence, the hypervariable regions CDR1, CDR2 and CDR3 and the constant part or fragment thereof of a human heavy chain; said CDR1 having the amino acid sequence SEQ ID NO:1, said CDR2 having the amino acid sequence SEQ ID NO:2, and said CDR3 having the amino acid sequence SEQ ID NO:3; and b) an immunoglobulin light chain or fragment thereof which comprises a variable domain comprising, in sequence, the hypervariable regions CDR1', CDR2', and CDR3' and the constant part or fragment thereof of a human light chain, said CDR1' having the amino acid sequence SEQ ID NO:4, said CDR2' having the amino acid sequence SEQ ID NO:5, and said CDR3' having the amino acid sequence SEQ ID NO:6.

In one embodiment, the IL-17 antibody or antigen-binding fragment thereof is selected from a single chain antibody or antigen-binding fragment thereof that comprises an antigen-binding site comprising: a) a first domain comprising, in sequence, the hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3; and b) a second domain comprising, in sequence, the hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6; and c) a peptide linker which is bound either to the N-terminal extremity of the first domain and to the C-terminal extremity of the second domain or to the C-terminal extremity of the first domain and to the N-terminal extremity of the second domain.

Alternatively, an IL-17 antibody or antigen-binding fragment thereof as used in the disclosed methods may comprise a derivative of the IL-17 antibodies set forth herein by sequence (e.g., a pegylated version of secukinumab or CJM112). Alternatively, the V$_H$ or V$_L$ domain of an IL-17 antibody or antigen-binding fragment thereof used in the disclosed methods may have V$_H$ or V$_L$ domains that are substantially identical to the V$_H$ or V$_L$ domains set forth in SEQ ID NO:8 and 10. A human IL-17 antibody disclosed herein may comprise a heavy chain that is substantially identical to that set forth as SEQ ID NO:15 and/or a light chain that is substantially identical to that set forth as SEQ ID NO:14. A human IL-17 antibody disclosed herein may comprise a heavy chain that comprises SEQ ID NO:15 and a light chain that comprises SEQ ID NO:14. A human IL-17 antibody disclosed herein may comprise: a) one heavy chain, comprising a variable domain having an amino acid sequence substantially identical to that shown in SEQ ID NO:8 and the constant part of a human heavy chain; and b) one light chain, comprising a variable domain having an amino acid sequence substantially identical to that shown in SEQ ID NO:10 and the constant part of a human light chain.

Alternatively, an IL-17 antibody or antigen-binding fragment thereof used in the disclosed methods may be an amino acid sequence variant of the reference IL-17 antibodies set forth herein, as long as it contains CysL97. The disclosure also includes IL-17 antibodies or antigen-binding fragments thereof (e.g., secukinumab) in which one or more of the amino acid residues of the V$_H$ or V$_L$ domain of secukinumab (but not CysL97), typically only a few (e.g., 1-10), are changed; for instance by mutation, e.g., site directed mutagenesis of the corresponding DNA sequences. In all such cases of derivative and variants, the IL-17 antibody or antigen-binding fragment thereof is capable of inhibiting the activity of about 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50%, said inhibitory activity being measured on IL-6 production induced by hu-IL-17 in human dermal fibroblasts as described in Example 1 of WO 2006/013107.

In some embodiments, the IL-17 antibodies or antigen-binding fragments thereof, e.g., secukinumab, bind to an epitope of mature human IL-17 comprising Leu74, Tyr85, His86, Met87, Asn88, Val124, Thr125, Pro126, 1le127, Val128, His129. In some embodiments, the IL-17 antibody, e.g., secukinumab, binds to an epitope of mature human IL-17 comprising Tyr43, Tyr44, Arg46, Ala79, Asp80. In some embodiments, the IL-17 antibody, e.g., secukinumab, binds to an epitope of an IL-17 homodimer having two mature human IL-17 chains, said epitope comprising Leu74, Tyr85, His86, Met87, Asn88, Val124, Thr125, Pro126, 1le127, Val128, His129 on one chain and Tyr43, Tyr44, Arg46, Ala79, Asp80 on the other chain. The residue numbering scheme used to define these epitopes is based on residue one being the first amino acid of the mature protein (i.e., IL-17A lacking the 23 amino acid N-terminal signal peptide and beginning with Glycine). The sequence for immature IL-17A is set forth in the Swiss-Prot entry Q16552. In some embodiments, the IL-17 antibody has a $K_D$ of about 100-200 pM. In some embodiments, the IL-17 antibody has an $IC_{50}$ of about 0.4 nM for in vitro neutralization of the biological activity of about 0.67 nM human IL-17A. In some embodiments, the absolute bioavailability of subcutaneously (SC) administered IL-17 antibody has a range of about 60-about 80%, e.g., about 76%. In some embodiments, the IL-17 antibody, such as secukinumab, has an elimination half-life of about 3-5 weeks, e.g., about 4 weeks (e.g., about 23 to about 35 days, about 23 to about 30 days, e.g., about 30 days). In some embodiments, the IL-17 antibody (such as secukinumab) has a $T_{max}$ of about 7-8 days.

2. CJM112

For ease of reference, the amino acid sequences of the hypervariable regions of the CJM112 monoclonal antibody, based on the Kabat definition and the Chothia definition, as well as the $V_L$ and $V_H$ domains and full heavy and light chains are provided in Table 2, below.

TABLE 2

Amino acid sequences of the hypervariable regions (CDRs), variable domains (VH and VL) and full chains of CJM112. The DNA encoding the VL of CJM112 is set forth in SEQ ID NO: 36. The DNA encoding the VH of CJM112 is set forth in SEQ ID NO: 34.

| CJM112 Light-Chain | | |
|---|---|---|
| CDR1 | Kabat | SEQ ID NO: 16 |
| | Chothia | SEQ ID NO: 17 |
| CDR2 | Kabat | SEQ ID NO: 18 |
| | Chothia | SEQ ID NO: 19 |
| CDR3 | Kabat | SEQ ID NO: 20 |
| | Chothia | SEQ ID NO: 21 |
| VL | | SEQ ID NO: 22 |
| Light Chain | | SEQ ID NO: 23 |

TABLE 2-continued

Amino acid sequences of the hypervariable regions (CDRs), variable domains (VH and VL) and full chains of CJM112. The DNA encoding the VL of CJM112 is set forth in SEQ ID NO: 36. The DNA encoding the VH of CJM112 is set forth in SEQ ID NO: 34.

| CJM112 Heavy-Chain | | |
|---|---|---|
| CDR1 | Kabat | SEQ ID NO: 24 |
| | Chothia | SEQ ID NO: 25 |
| CDR2 | Kabat | SEQ ID NO: 26 |
| | Chothia | SEQ ID NO: 27 |
| CDR3 | Kabat | SEQ ID NO: 28 |
| | Chothia | SEQ ID NO: 29 |
| VH | | SEQ ID NO: 30 |
| Heavy Chain | | SEQ ID NO: 31 |

In one embodiment, the IL-17 antibody or antigen-binding fragment thereof comprises at least one immunoglobulin heavy chain variable domain ($V_H$) comprising hypervariable regions CDR1, CDR2 and CDR3, said CDR1 having the amino acid sequence SEQ ID NO:24, said CDR2 having the amino acid sequence SEQ ID NO:26, and said CDR3 having the amino acid sequence SEQ ID NO:28. In one embodiment, the IL-17 antibody or antigen-binding fragment thereof comprises at least one immunoglobulin heavy chain variable domain ($V_H$) comprising hypervariable regions CDR1, CDR2 and CDR3, said CDR1 having the amino acid sequence SEQ ID NO:25, said CDR2 having the amino acid sequence SEQ ID NO:27, and said CDR3 having the amino acid sequence SEQ ID NO:29.

In one embodiment, the IL-17 antibody or antigen-binding fragment thereof comprises at least one immunoglobulin light chain variable domain ($V_L$) comprising hypervariable regions CDR1, CDR2 and CDR3, said CDR1 having the amino acid sequence SEQ ID NO:16, said CDR2 having the amino acid sequence SEQ ID NO:18 and said CDR3 having the amino acid sequence SEQ ID NO:20. In one embodiment, the IL-17 antibody or antigen-binding fragment thereof comprises at least one immunoglobulin light chain variable domain ($V_L$) comprising hypervariable regions CDR1, CDR2 and CDR3, said CDR1 having the amino acid sequence SEQ ID NO:17, said CDR2 having the amino acid sequence SEQ ID NO:19 and said CDR3 having the amino acid sequence SEQ ID NO:21.

In one embodiment, the IL-17 antibody or antigen-binding fragment thereof comprises at least one immunoglobulin $V_H$ domain and at least one immunoglobulin $V_L$ domain, wherein: a) the immunoglobulin $V_H$ domain comprises (e.g., in sequence): i) hypervariable regions CDR1, CDR2 and CDR3, said CDR1 having the amino acid sequence SEQ ID NO:24, said CDR2 having the amino acid sequence SEQ ID NO:26, and said CDR3 having the amino acid sequence SEQ ID NO:28; or ii) hypervariable regions CDR1, CDR2 and CDR3, said CDR1 having the amino acid sequence SEQ ID NO:25, said CDR2 having the amino acid sequence SEQ ID NO:27, and said CDR3 having the amino acid sequence SEQ ID NO:29; and b) the immunoglobulin $V_L$ domain comprises (e.g., in sequence): i) hypervariable regions CDR1, CDR2 and CDR3, said CDR1 having the amino acid sequence SEQ ID NO:16, said CDR2 having the amino acid sequence SEQ ID NO:18, and said CDR3 having the amino acid sequence SEQ ID NO:20 or ii) hypervariable regions CDR1, CDR2 and CDR3, said CDR1 having the amino acid sequence SEQ ID NO:17, said CDR2 having the amino acid sequence SEQ ID NO:19, and said CDR3 having the amino acid sequence SEQ ID NO:21.

In one embodiment, the IL-17 antibody or antigen-binding fragment thereof comprises: a) an immunoglobulin heavy chain variable domain ($V_H$) comprising the amino acid sequence set forth as SEQ ID NO:30; b) an immunoglobulin light chain variable domain ($V_L$) comprising the amino acid sequence set forth as SEQ ID NO:22; c) an immunoglobulin $V_H$ domain comprising the amino acid sequence set forth as SEQ ID NO:30 and an immunoglobulin $V_L$ domain comprising the amino acid sequence set forth as SEQ ID NO:22; d) an immunoglobulin $V_H$ domain comprising the hypervariable regions set forth as SEQ ID NO:24, SEQ ID NO:26, and SEQ ID NO:28; e) an immunoglobulin $V_L$ domain comprising the hypervariable regions set forth as SEQ ID NO:16, SEQ ID NO:18 and SEQ ID NO:20; f) an immunoglobulin $V_H$ domain comprising the hypervariable regions set forth as SEQ ID NO:25, SEQ ID NO:27 and SEQ ID NO:29; g) an immunoglobulin $V_L$ domain comprising the hypervariable regions set forth as SEQ ID NO:17, SEQ ID NO:19 and SEQ ID NO:21; h) an immunoglobulin $V_H$ domain comprising the hypervariable regions set forth as SEQ ID NO:24, SEQ ID NO:26, and SEQ ID NO:28 and an immunoglobulin $V_L$ domain comprising the hypervariable regions set forth as SEQ ID NO:16, SEQ ID NO:18 and SEQ ID NO:20; i) an immunoglobulin $V_H$ domain comprising the hypervariable regions set forth as SEQ ID NO:25, SEQ ID NO:27, and SEQ ID NO:29 and an immunoglobulin $V_L$ domain comprising the hypervariable regions set forth as SEQ ID NO:17, SEQ ID NO:19 and SEQ ID NO:21; j) a light chain comprising SEQ ID NO:23; k) a heavy chain comprising SEQ ID NO:31; or l) a light chain comprising SEQ ID NO:23 and a heavy chain comprising SEQ ID NO:31.

In some embodiments, the IL-17 antibody or antigen-binding fragment thereof (e.g., CJM112) comprises the three CDRs of SEQ ID NO:22. In other embodiments, the IL-17 antibody or antigen-binding fragment thereof comprises the three CDRs of SEQ ID NO:30. In other embodiments, the IL-17 antibody or antigen-binding fragment thereof comprises the three CDRs of SEQ ID NO:22 and the three CDRs of SEQ ID NO:30. In some embodiments, the IL-17 antibody or antigen-binding fragment thereof comprises the three CDRs of SEQ ID NO:23. In other embodiments, IL-17 antibody or antigen-binding fragment thereof comprises the three CDRs of SEQ ID NO:31. In other embodiments, the IL-17 antibody or antigen-binding fragment thereof comprises the three CDRs of SEQ ID NO:23 and the three CDRs of SEQ ID NO:31.

In one embodiment, the IL-17 antibody or antigen-binding fragment thereof (e.g., CJM112) is selected from a human IL-17 antibody that comprises at least: a) an immunoglobulin heavy chain or fragment thereof which comprises a variable domain comprising, in sequence, the hypervariable regions CDR1, CDR2 and CDR3 and the constant part or fragment thereof of a human heavy chain; said CDR1 having the amino acid sequence SEQ ID NO:24, said CDR2 having the amino acid sequence SEQ ID NO:26, and said CDR3 having the amino acid sequence SEQ ID NO:28; and b) an immunoglobulin light chain or fragment thereof which comprises a variable domain comprising, in sequence, the hypervariable regions CDR1, CDR2, and CDR3 and the constant part or fragment thereof of a human light chain, said CDR1 having the amino acid sequence SEQ ID NO:16, said CDR2 having the amino acid sequence SEQ ID NO:18, and said CDR3 having the amino acid sequence SEQ ID NO:20.

In one embodiment, the IL-17 antibody or antigen-binding fragment thereof (e.g., CJM112) is selected from a human IL-17 antibody that comprises at least: a) an immunoglobulin heavy chain or fragment thereof which comprises a variable domain comprising, in sequence, the hypervariable regions CDR1, CDR2 and CDR3 and the constant part or fragment thereof of a human heavy chain; said CDR1 having the amino acid sequence SEQ ID NO:25, said CDR2 having the amino acid sequence SEQ ID NO:27 and said CDR3 having the amino acid sequence SEQ ID NO:29; and b) an immunoglobulin light chain or fragment thereof which comprises a variable domain comprising, in sequence, the hypervariable regions CDR1, CDR2, and CDR3 and the constant part or fragment thereof of a human light chain, said CDR1 having the amino acid sequence SEQ ID NO:17, said CDR2 having the amino acid sequence SEQ ID NO:19, and said CDR3 having the amino acid sequence SEQ ID NO:21.

In one embodiment, the IL-17 antibody or antigen-binding fragment thereof is selected from a single chain antibody or antigen-binding fragment thereof that comprises an antigen-binding site comprising: a) a first domain comprising, in sequence, the hypervariable regions CDR1, CDR2 and CDR3, said CDR1 having the amino acid sequence SEQ ID NO:24, said CDR2 having the amino acid sequence SEQ ID NO:26, and said CDR3 having the amino acid sequence SEQ ID NO:28; and b) a second domain comprising, in sequence, the hypervariable regions CDR1, CDR2 and CDR3, said CDR1 having the amino acid sequence SEQ ID NO:16, said CDR2 having the amino acid sequence SEQ ID NO:18, and said CDR3 having the amino acid sequence SEQ ID NO:20; and c) a peptide linker which is bound either to the N-terminal extremity of the first domain and to the C-terminal extremity of the second domain or to the C-terminal extremity of the first domain and to the N-terminal extremity of the second domain.

In one embodiment, the IL-17 antibody or antigen-binding fragment thereof (e.g., CJM112) is selected from a single chain antibody or antigen-binding fragment thereof that comprises an antigen-binding site comprising: a) a first domain comprising, in sequence, the hypervariable regions CDR1, CDR2 and CDR3, said CDR1 having the amino acid sequence SEQ ID NO:25, said CDR2 having the amino acid sequence SEQ ID NO:27, and said CDR3 having the amino acid sequence SEQ ID NO:29; and b) a second domain comprising, in sequence, the hypervariable regions CDR1, CDR2 and CDR3, said CDR1 having the amino acid sequence SEQ ID NO:17, said CDR2 having the amino acid sequence SEQ ID NO:19, and said CDR3 having the amino acid sequence SEQ ID NO:21; and c) a peptide linker which is bound either to the N-terminal extremity of the first domain and to the C-terminal extremity of the second domain or to the C-terminal extremity of the first domain and to the N-terminal extremity of the second domain.

The $V_H$ or $V_L$ domain of an IL-17 antibody or antigen-binding fragment thereof used in the disclosed methods may have $V_H$ and/or $V_L$ domains that are substantially identical to the $V_H$ or $V_L$ domains set forth in SEQ ID NO:22 and 30. A human IL-17 antibody disclosed herein may comprise a heavy chain that is substantially identical to that set forth as SEQ ID NO:31 and/or a light chain that is substantially identical to that set forth as SEQ ID NO:23. A human IL-17 antibody disclosed herein may comprise a heavy chain that comprises SEQ ID NO:31 and a light chain that comprises SEQ ID NO:23. A human IL-17 antibody disclosed herein may comprise: a) one heavy chain, comprising a variable domain having an amino acid sequence substantially identical to that shown in SEQ ID NO:30 and the constant part of a human heavy chain; and b) one light chain, comprising a variable domain having an amino acid sequence substantially identical to that shown in SEQ ID NO:22 and the constant part of a human light chain.

In some embodiments of the disclosed uses, methods and kits, the IL-17 antibody or antigen-binding fragment thereof binds to an epitope of IL-17 between residues Arg 55 and Trp 67, e.g., an epitope comprising Arg 55, Glu 57, and Trp 67. In some embodiments of the disclosed uses, methods and kits, the IL-17 antibody or antigen-binding fragment thereof binds to an epitope comprising: Arg 55, Glu 57, Trp 67, Tyr 62, and Arg 101; Arg 55, Glu 57, Trp 67, Tyr 62, Arg 101, Pro 59, Ser 64, and Val 65; Arg 55, Glu 57, Trp 67, Tyr 62, Arg 101, Pro 59, Ser 64, Val 65, Val 22*, Leu 26, Asp 58, Glu 60, Pro 63, Pro 107, Phe 110, and Lys 114*, where amino acids marked with (*) designate residue contributed by the second IL-17 subunit of the homodimer IL-17A. The residue numbering scheme used to define these epitopes is based on residue one being the first amino acid of the mature protein (i.e., IL-17A lacking the 23 amino acid N-terminal signal peptide and beginning with Glycine). The sequence for immature IL-17A is set forth in the Swiss-Prot entry Q16552.

In some embodiments, the IL-17 antibody or antigen-binding fragment thereof has a $K_D$ for human IL-17 of about 1-10 pM (e.g., about 6 pM). In some embodiments, the IL-17 antibody or antigen-binding fragment thereof has an in vivo half-life of about 2-4 weeks, e.g., about 3 weeks.

Other preferred IL-17 antagonists (e.g., antibodies) for use in the disclosed methods, kits and regimens are those set forth in U.S. Pat. Nos. 8,057,794; 7,767,206; 8,003,099; 8,110,191; and 7,838,638 and US Published Patent Application Nos: 20120034656 and 20110027290, which are incorporated by reference herein in their entirety.

Methods of Treatment and Uses of IL-17 Antagonists for Asthma

The disclosed IL-17 antagonists, e.g., IL-17 binding molecules (e.g., IL-17 antibody or antigen-binding fragment thereof, e.g., secukinumab or CJM112) or IL-17 receptor binding molecules (e.g., IL-17 receptor antibody or antigen-binding fragment thereof), may be used in vitro, ex vivo, or incorporated into pharmaceutical compositions and administered in vivo to treat asthma, e.g., moderate to severe asthma (e.g., human patients having asthma).

The IL-17 antagonists, e.g., IL-17 binding molecules (e.g., IL-17 antibody or antigen-binding fragment thereof, e.g., secukinumab or CJM112) or IL-17 receptor binding molecules (e.g., IL-17 receptor antibody or antigen-binding fragment thereof), may be used as a pharmaceutical composition when combined with a pharmaceutically acceptable carrier. Such a composition may contain, in addition to an IL-17 antagonist, carriers, various diluents, fillers, salts, buffers, stabilizers, solubilizers, and other materials well known in the art. The characteristics of the carrier will depend on the route of administration. The pharmaceutical compositions for use in the disclosed methods may also contain additional therapeutic agents for treatment of the particular targeted disorder. For example, a pharmaceutical composition may also include anti-inflammatory agents. Such additional factors and/or agents may be included in the pharmaceutical composition to produce a synergistic effect with the IL-17 binding molecules, or to minimize side effects caused by the IL-17 antagonists, e.g., IL-17 binding molecules (e.g., IL-17 antibody or antigen-binding fragment thereof, e.g., secukinumab or CJM112) or IL-17 receptor binding molecules (e.g., IL-17 antibody or antigen-binding fragment thereof).

Pharmaceutical compositions for use in the disclosed methods may be manufactured in conventional manner. In one embodiment, the pharmaceutical composition is provided in lyophilized form. For immediate administration it is dissolved in a suitable aqueous carrier, for example sterile water for injection or sterile buffered physiological saline. If it is considered desirable to make up a solution of larger volume for administration by infusion rather than a bolus injection, may be advantageous to incorporate human serum albumin or the patient's own heparinized blood into the saline at the time of formulation. The presence of an excess of such physiologically inert protein prevents loss of antibody by adsorption onto the walls of the container and tubing used with the infusion solution. If albumin is used, a suitable concentration is from 0.5 to 4.5% by weight of the saline solution. Other formulations comprise liquid or lyophilized formulation.

Antibodies, e.g., antibodies to IL-17, are typically formulated either in aqueous form ready for parenteral administration or as lyophilisate for reconstitution with a suitable diluent prior to administration. In some embodiments of the disclosed methods and uses, the IL-17 antagonist, e.g., IL-17 antibody, e.g., secukinumab or CJM112, is formulated as a lyophilisate. Suitable lyophilisate formulations can be reconstituted in a small liquid volume (e.g., 2 ml or less) to allow subcutaneous administration and can provide solutions with low levels of antibody aggregation. The use of antibodies as the active ingredient of pharmaceuticals is now widespread, including the products HERCEPTIN™ (trastuzumab), RITUXAN™ (rituximab), SYNAGIS™ (palivizumab), etc. Techniques for purification of antibodies to a pharmaceutical grade are well known in the art. When a therapeutically effective amount of an IL-17 antagonist, e.g., IL-17 binding molecules (e.g., IL-17 antibody or antigen-binding fragment thereof, e.g., secukinumab or CJM112) or IL-17 receptor binding molecules (e.g., IL-17 antibody or antigen-binding fragment thereof) is administered by intravenous, cutaneous or subcutaneous injection, the IL-17 antagonist will be in the form of a pyrogen-free, parenterally acceptable solution. A pharmaceutical composition for intravenous, cutaneous, or subcutaneous injection may contain, in addition to the IL-17 antagonist, an isotonic vehicle such as sodium chloride, Ringer's solution, dextrose, dextrose and sodium chloride, lactated Ringer's solution, or other vehicle as known in the art.

The appropriate dosage will vary depending upon, for example, the particular IL-17 antagonists, e.g., IL-17 binding molecules (e.g., IL-17 antibody or antigen-binding fragment thereof, e.g., secukinumab or CJM112) or IL-17 receptor binding molecules (e.g., IL-17 antibody or antigen-binding fragment thereof) to be employed, the host, the mode of administration and the nature and severity of the condition being treated, and on the nature of prior treatments that the patient has undergone. Ultimately, the attending health care provider will decide the amount of the IL-17 antagonist with which to treat each individual patient. In some embodiments, the attending health care provider may administer low doses of the IL-17 antagonist and observe the patient's response. In other embodiments, the initial dose(s) of IL-17 antagonist administered to a patient are high, and then are titrated downward until signs of relapse occur. Larger doses of the IL-17 antagonist may be administered until the optimal therapeutic effect is obtained for the patient, and the dosage is not generally increased further.

In practicing some of the methods of treatment or uses of the present disclosure, a therapeutically effective amount of an IL-17 antagonist, e.g., IL-17 binding molecule (e.g., IL-17 antibody or antigen-binding fragment thereof, e.g., secukinumab or CJM112) or IL-17 receptor binding molecule (e.g., IL-17 antibody or antigen-binding fragment thereof) is administered to a patient, e.g., a mammal (e.g., a human). While it is understood that the disclosed methods provide for treatment of asthma patients using an IL-17 antagonist (e.g., secukinumab or CJM112), this does not preclude that, if the patient is to be ultimately treated with an IL-17 antagonist, such IL-17 antagonist therapy is necessarily a monotherapy. Indeed, if a patient is selected for treatment with an IL-17 antagonist, then the IL-17 antagonist (e.g., secukinumab or CJM112) may be administered in accordance with the methods of the disclosure either alone or in combination with other agents and therapies for treating asthma patients, e.g., in combination with at least one additional asthma agent or asthma treatment, such as Long-acting beta agonist (LABA) and Long-acting antimuscarinic agent (LAMA), medium to high dose inhaled glucocorticoid, and leukotriene receptor antagonist.

When co-administered with one or more additional asthma agents, an IL-17 antagonist may be administered either simultaneously with the other agent, or sequentially. If administered sequentially, the attending physician will decide on the appropriate sequence of administering the IL-17 antagonist in combination with other agents and the appropriate dosages for co-delivery. An IL-17 antagonist, e.g., IL-17 binding molecule (e.g., IL-17 antibody or antigen-binding fragment thereof, e.g., secukinumab or CJM112) or IL-17 receptor binding molecule (e.g., IL-17 receptor antibody or antigen-binding fragment thereof) is conveniently administered parenterally, e.g., intravenously (e.g., into the antecubital or other peripheral vein), intramuscularly, or subcutaneously. The duration of intravenous (IV) therapy using a pharmaceutical composition of the present disclosure will vary, depending on the severity of the disease being treated and the condition and personal response of each individual patient. Also contemplated is subcutaneous (SC) therapy using a pharmaceutical composition of the present disclosure. The health care provider will decide on the appropriate duration of IV or SC therapy and the timing of administration of the therapy, using the pharmaceutical composition of the present disclosure.

The IL-17 antagonist, e.g., IL-17 binding molecule (e.g., IL-17 antibody or antigen-binding fragment thereof, e.g., secukinumab or CJM112) or IL-17 receptor binding molecule (e.g., IL-17 receptor antibody or antigen-binding fragment thereof) may be administered to the asthma patient as part of a loading regimen (an initial regimen designed to deliver drug quickly to target tissue—typically using more frequent dosing than employed for maintenance, but also sometimes using higher doses than employed for maintenance). For example, a loading regimen may employ SC dosing of about 75 mg-about 600 mg (e.g., about 75 mg, about 150 mg, about 300 mg, about 450 mg, about 600 mg) of the IL-17 antibody (e.g., CJM112, secukinumab) weekly during weeks 0, 1, 2, 3, and 4. Thereafter, a maintenance regimen is employed, and the patient is administered the IL-17 antibody at about 75 mg-about 600 mg (e.g., about 75 mg, about 150 mg, about 300 mg, about 450 mg, about 600 mg) monthly. As a result, the patient is dosed SC with about 75 mg-about 600 mg (e.g., about 75 mg, about 150 mg, about 300 mg, about 450 mg, about 600 mg) of the IL-17 antagonist (e.g., secukinumab or CJM112) during weeks 0, 1, 2, 3, 4, 8, 12, 16, 20, etc. Maintenance dosing may be less frequent than monthly, e.g., every other month, quarterly, bi-yearly, etc., which typically accompanies a higher of drug, e.g., 450 mg, 600 mg, etc.

Alternatively, the IL-17 antagonist, e.g., IL-17 binding molecule (e.g., IL-17 antibody or antigen-binding fragment thereof, e.g., secukinumab or CJM112) or IL-17 receptor binding molecule (e.g., IL-17 receptor antibody or antigen-binding fragment thereof) may be administered to the asthma patient without a loading regimen, e.g., the antagonist may be administered to the patient SC at about 75 mg-about 600 mg (e.g., about 75 mg, about 150 mg, about 300 mg, about 450 mg, about 600 mg) every 4 weeks (monthly). In this manner, the patient is dosed SC with about 75 mg-about 600 mg (e.g., about 75 mg, about 150 mg, about 300 mg, about 450 mg, about 600 mg) of the IL-17 antagonist (e.g., secukinumab or CJM112) during weeks 0, 4, 8, 12, 16, 20, etc. Dosing may be less frequent than monthly, e.g., every other month, quarterly, bi-yearly, etc., which typically accompanies a higher of drug, e.g., 450 mg, 600 mg, etc. In a preferred embodiment, the IL-17 antagonist is CJM112, which is administered without a loading regimen; preferably CJM112 is administered to the patient SC at about 75 mg-about 600 mg (e.g., about 75 mg, about 150 mg, about 300 mg, about 450 mg, about 600 mg) every 4 weeks (monthly). A typical duration of treatment is about 12 to about 24 weeks, although both shorter and longer courses of treatment may be employed, depending on a patient's response to therapy.

Alternatively, the IL-17 antagonist, e.g., IL-17 binding molecule (e.g., IL-17 antibody or antigen-binding fragment thereof, e.g., secukinumab or CJM112) or IL-17 receptor binding molecule (e.g., IL-17 receptor antibody or antigen-binding fragment thereof) may be administered to the asthma patient as a single dose, e.g., the antagonist may be administered to the patient SC at about 150 mg-about 600 mg (e.g., about 150 mg, about 300 mg, about 450 mg, about 600 mg) once. In this manner, the patient is dosed SC with about 150 mg-about 600 mg (e.g., about 150 mg, about 300 mg, about 450 mg, about 600 mg) of the IL-17 antagonist (e.g., secukinumab or CJM112) only one time. The patient would then be dosed again only when asthma symptoms recur.

It will be understood that dose escalation may be appropriate for certain asthma patients, e.g., patients that display inadequate response to treatment with the IL-17 antagonists, e.g., IL-17 binding molecules (e.g., IL-17 antibody or antigen-binding fragment thereof, e.g., secukinumab and CJM112) or IL-17 receptor binding molecules (e.g., IL-17 receptor antibody or antigen-binding fragment thereof). Thus, SC dosages may be greater than about 75 mg to about 300 mg SC, e.g., about 80 mg, about 100 mg, about 125 mg, about 175 mg, about 200 mg, about 250 mg, about 350 mg, about 400 mg, about 450 mg, about 500 mg, about 600 mg, etc.; similarly, IV dosages may be greater than about 10 mg/kg, e.g., about 11 mg/kg, 12 mg/kg, 15 mg/kg, 20 mg/kg, 25 mg/kg, 30 mg/kg, 35 mg/kg, etc. It will also be understood that dose reduction may also be appropriate for certain asthma patients, e.g., patients that display adverse events or an adverse response to treatment with the IL-17 antagonist (e.g., IL-17 antibody or antigen-binding fragment thereof, e.g., secukinumab or CJM112). Thus, dosages of the IL-17 antagonist (e.g., IL-17 antibody or antigen-binding fragment thereof, e.g., secukinumab or CJM112), may be less than about 75 mg to about 300 mg SC, e.g., about 25 mg, about 50 mg, about 80 mg, about 100 mg, about 125 mg, about 175 mg, about 200 mg, 250 mg, etc. In some embodiments, the IL-17 antagonist, e.g., IL-17 binding molecule (e.g., IL-17 antibody or antigen-binding fragment thereof, e.g., secukinumab or CJM112) or IL-17 receptor binding molecule (e.g., IL-17 receptor antibody or antigen-binding fragment thereof) may be administered to the patient at an initial dose of 75 mg delivered SC, and the dose may be then escalated to 150 mg or 300 mg if needed, as determined by a physician. In some embodiments, the IL-17 antagonist, e.g., IL-17 binding molecule (e.g., IL-17 antibody or antigen-binding fragment thereof, e.g., secukinumab or CJM112) or IL-17 receptor binding molecule (e.g., IL-17 receptor antibody or antigen-binding fragment thereof) may be administered to the patient at an initial dose of 150 mg or 300 mg delivered SC, and the dose may be then escalated to 450 mg or 600 mg if needed, as determined by a physician.

Disclosed herein are methods of treating asthma, comprising administering an IL-17 antagonist to a patient in need thereof. In some embodiments, the IL-17 antagonist is an IL-17 antibody or antigen-binding fragment thereof.

Additionally disclosed herein are methods of treating a patient having asthma, e.g., moderate to severe asthma, comprising administering an IL-17 antibody or antigen-binding fragment thereof to a patient in need thereof, wherein the IL-17 antibody or antigen-binding fragment thereof binds to an epitope of mature IL-17: a) between residues Arg 55 and Trp 67; b) comprising Arg 55, Glu 57, and Trp 67; c) comprising Arg 55, Glu 57, Trp 67, Tyr 62, and Arg 101; d) comprising Arg 55, Glu 57, Trp 67, Tyr 62, Arg 101, Pro 59, Ser 64, and Val 65; or e) comprising Arg 55, Glu 57, Trp 67, Tyr 62, Arg 101, Pro 59, Ser 64, Val 65, Val 22*, Leu 26, Asp 58, Glu 60, Pro 63, Pro 107, Phe 110, and Lys 114*, where amino acids marked with (*) designate a residue contributed by the second IL-17 subunit of the IL-17A homodimer), wherein the IL-17 antibody or antigen-binding fragment thereof has a $K_D$ for human IL-17 of about 1-10 pM (e.g., about 6 pM) and an in vivo half-life of about 2-4 weeks, e.g., about 3 weeks.

Additionally disclosed herein are IL-17 antagonists (e.g., IL-17 antibody or antigen-binding fragment thereof, e.g., CJM112) for use in treating a patient having asthma, e.g., moderate to severe asthma, wherein the IL-17 antibody or antigen-binding fragment thereof binds to an epitope of mature IL-17: a) between residues Arg 55 and Trp 67; b) comprising Arg 55, Glu 57, and Trp 67; c) comprising Arg 55, Glu 57, Trp 67, Tyr 62, and Arg 101; d) comprising Arg 55, Glu 57, Trp 67, Tyr 62, Arg 101, Pro 59, Ser 64, and Val 65; or e) comprising Arg 55, Glu 57, Trp 67, Tyr 62, Arg 101, Pro 59, Ser 64, Val 65, Val 22*, Leu 26, Asp 58, Glu 60, Pro 63, Pro 107, Phe 110, and Lys 114*, where amino acids marked with (*) designate a residue contributed by the second IL-17 subunit of the IL-17A homodimer), wherein the IL-17 antibody or antigen-binding fragment thereof has a $K_D$ for human IL-17 of about 1-10 pM (e.g., about 6 pM) and an in vivo half-life of about 2-4 weeks, e.g., about 3 weeks.

Additionally disclosed herein are IL-17 antagonists (e.g., IL-17 antibody or antigen-binding fragment thereof, e.g., CJM112) for use in the manufacture of a medicament for treating a patient having asthma, e.g., moderate to severe asthma, wherein the IL-17 antibody or antigen-binding fragment thereof binds to an epitope of mature IL-17: a) between residues Arg 55 and Trp 67; b) comprising Arg 55, Glu 57, and Trp 67; c) comprising Arg 55, Glu 57, Trp 67, Tyr 62, and Arg 101; d) comprising Arg 55, Glu 57, Trp 67, Tyr 62, Arg 101, Pro 59, Ser 64, and Val 65; or e) comprising Arg 55, Glu 57, Trp 67, Tyr 62, Arg 101, Pro 59, Ser 64, Val 65, Val 22*, Leu 26, Asp 58, Glu 60, Pro 63, Pro 107, Phe 110, and Lys 114*, where amino acids marked with (*) designate a residue contributed by the second IL-17 subunit of the IL-17A homodimer), wherein the IL-17 antibody or antigen-binding fragment thereof has a $K_D$ for human IL-17 of about 1-10 pM (e.g., about 6 pM) and an in vivo half-life of about 2-4 weeks, e.g., about 3 weeks.

Additionally disclosed herein are IL-17 antagonists (e.g., IL-17 antibody or antigen-binding fragment thereof, e.g., secukinumab or CJM112) for use in the manufacture of a medicament for treating a patient having asthma, e.g., moderate to severe asthma wherein the patient is to be selected based on having a total serum concentration of IgE below a threshold of 300, 250, 200,150, or 100 IU/mL, preferably below 300 IU/mL, and most preferably below a threshold of 150 IU/mL, and optionally, an eosinophil count in peripheral blood below 300 per µL, wherein the medicament is formulated to comprise containers, each container having a sufficient amount of the IL-17 antagonist (e.g., IL-17 antibody or antigen-binding fragment thereof, e.g., secukinumab or CJM112) to allow subcutaneous delivery of at least about 75 mg-about 600 mg (e.g., about 75 mg, about 150 mg, about 300 mg, about 450 mg, about 600 mg), preferably about 75 mg-about 300 mg, of the IL-17 antagonist (e.g., IL-17 antibody or antigen-binding fragment thereof, e.g., secukinumab or CJM112) per unit dose, and further wherein the IL-17 antibody or antigen-binding fragment thereof binds to an epitope of mature IL-17: a) between residues Arg 55 and Trp 67; b) comprising Arg 55, Glu 57, and Trp 67; c) comprising Arg 55, Glu 57, Trp 67, Tyr 62, and Arg 101; d) comprising Arg 55, Glu 57, Trp 67, Tyr 62, Arg 101, Pro 59, Ser 64, and Val 65; or e) comprising Arg 55, Glu 57, Trp 67, Tyr 62, Arg 101, Pro 59, Ser 64, Val 65, Val 22*, Leu 26, Asp 58, Glu 60, Pro 63, Pro 107, Phe 110, and Lys 114*, where amino acids marked with (*) designate a residue contributed by the second IL-17 subunit of the IL-17A homodimer), wherein the IL-17 antibody or antigen-binding fragment thereof has a $K_D$ for human IL-17 of about 1-10 pM (e.g., about 6 pM) and an in vivo half-life of about 2-4 weeks, e.g., about 3 weeks.

Disclosed herein are methods of treating a patient having asthma, e.g., moderate to severe asthma, comprising administering an IL-17 antibody or antigen-binding fragment thereof to a patient in need thereof, wherein the IL-17 antibody or antigen-binding fragment thereof binds to an epitope of an IL-17 homodimer having two mature IL-17 protein chains, said epitope comprising Leu74, Tyr85, His86, Met87, Asn88, Val124, Thr125, Pro126, 11e127, Val128, His129 on one chain and Tyr43, Tyr44, Arg46, Ala79, Asp80 on the other chain, wherein the IL-17 antibody or antigen-binding fragment thereof has a $K_D$ for human IL-17 of about 100-200 pM, and wherein the IL-17 antibody or antigen-binding fragment thereof has an in vivo half-life of about 4 weeks.

Additionally disclosed herein are IL-17 antagonists (e.g., IL-17 antibody or antigen-binding fragment thereof, e.g., secukinumab or CJM112) for use in treating a patient having asthma, e.g., moderate to severe asthma, wherein the IL-17 antagonist (e.g., IL-17 antibody or antigen-binding fragment thereof, e.g., secukinumab or CJM112) binds to an epitope of an IL-17 homodimer having two mature IL-17 protein chains, said epitope comprising Leu74, Tyr85, His86, Met87, Asn88, Val124, Thr125, Pro126, 11e127, Val128, His129 on one chain and Tyr43, Tyr44, Arg46, Ala79, Asp80 on the other chain, wherein the IL-17 antibody or antigen-binding fragment thereof has a $K_D$ for human IL-17 of about 100-200 pM, and wherein the IL-17 antibody or antigen-binding fragment thereof has an in vivo half-life of about 4 weeks.

Additionally disclosed herein are IL-17 antagonists (e.g., IL-17 antibody or antigen-binding fragment thereof, e.g., secukinumab or CJM112) for use in the manufacture of a medicament for treating a patient having asthma, e.g., moderate to severe asthma, wherein the IL-17 antagonist (e.g., IL-17 antibody or antigen-binding fragment thereof, e.g., secukinumab or CJM112) binds to an epitope of an IL-17 homodimer having two mature IL-17 protein chains, said epitope comprising Leu74, Tyr85, His86, Met87, Asn88, Va1124, Thr125, Pro126, 11e127, Va1128, His129 on one chain and Tyr43, Tyr44, Arg46, Ala79, Asp80 on the other chain, wherein the IL-17 antibody or antigen-binding fragment thereof has a $K_D$ for human IL-17 of about 100-200 pM, and wherein the IL-17 antibody or antigen-binding fragment thereof has an in vivo half-life of about 4 weeks.

Additionally disclosed herein are IL-17 antagonists (e.g., IL-17 antibody or antigen-binding fragment thereof, e.g., secukinumab or CJM112) for use in the manufacture of a medicament for treating a patient having asthma, e.g., moderate to severe asthma wherein the patient is to be selected based on having a total serum concentration of IgE below a threshold of 300, 250, 200,150, or 100 IU/mL, preferably below 300 IU/mL, and most preferably below a threshold of 150 IU/mL, and optionally, an eosinophil count in peripheral blood below 300 per µL, wherein the medicament is formulated to comprise containers, each container having a sufficient amount of the IL-17 antagonist (e.g., IL-17 antibody or antigen-binding fragment thereof, e.g., secukinumab or CJM112) to allow subcutaneous delivery of at least about 75 mg-about 300 mg (e.g., about 75 mg, about 150 mg, about 300 mg, about 450 mg, about 600 mg), preferably about 75 mg-about 300 mg, of the IL-17 antagonist (e.g., IL-17 antibody or antigen-binding fragment thereof, e.g., secukinumab or CJM112) per unit dose, and further wherein the IL-17 antagonist (e.g., IL-17 antibody or antigen-binding fragment thereof, e.g., secukinumab or CJM112) binds to an epitope of an IL-17 homodimer having two mature IL-17 protein chains, said epitope comprising Leu74, Tyr85, His86, Met87, Asn88, Va1124, Thr125, Pro126, 11e127, Va1128, His129 on one chain and Tyr43, Tyr44, Arg46, Ala79, Asp80 on the other chain, wherein the IL-17 antibody or antigen-binding fragment thereof has a $K_D$ for human IL-17 of about 100-200 pM, and wherein the IL-17 antibody or antigen-binding fragment thereof has an in vivo half-life of about 4 weeks.

Additionally disclosed herein are IL-17 antagonists (e.g., IL-17 antibody or antigen-binding fragment thereof, e.g., secukinumab or CJM112) for use in the manufacture of a medicament for selectively treating a patient having asthma, e.g., moderate to severe asthma, wherein the patient is to be selected based on having a total serum concentration of IgE below a threshold of 300, 250, 200,150, or 100 IU/mL, preferably below 300 IU/mL, and most preferably below a threshold of 150 IU/mL, and optionally, an eosinophil count in peripheral blood below 300 per µL, wherein the medicament is formulated at a dosage to allow subcutaneous delivery of at least about 75 mg-about 600 mg (e.g., about 75 mg, about 150 mg, about 300 mg, about 450 mg, about 600 mg), preferably about 75 mg-about 300 mg, of the IL-17 antagonist (e.g., IL-17 antibody or antigen-binding fragment thereof, e.g., secukinumab or CJM112) per unit dose, and further wherein the IL-17 antibody or antigen-binding fragment thereof binds to an epitope of mature IL-17: a) between residues Arg 55 and Trp 67; b) comprising Arg 55, Glu 57, and Trp 67; c) comprising Arg 55, Glu 57, Trp 67, Tyr 62, and Arg 101; d) comprising Arg 55, Glu 57, Trp 67, Tyr 62, Arg 101, Pro 59, Ser 64, and Val 65; or e) comprising Arg 55, Glu 57, Trp 67, Tyr 62, Arg 101, Pro 59, Ser 64, Val 65, Val 22*, Leu 26, Asp 58, Pro 63, Pro 107, Phe 110, and Lys 114*, where amino acids marked with (*) designate a residue contributed by the second IL-17 subunit of the IL-17A homodimer), wherein the IL-17 antibody or antigen-binding fragment thereof has a $K_D$ for human IL-17 of about 1-10 pM (e.g., about 6 pM) and an in vivo half-life of about 2-4 weeks, e.g., about 3 weeks.

Additionally disclosed herein are IL-17 antagonists (e.g., IL-17 antibody or antigen-binding fragment thereof, e.g., secukinumab or CJM112) for use in the manufacture of a medicament for selectively treating a patient having asthma, e.g., moderate to severe asthma, wherein the patient is to be selected based on having a total serum concentration of IgE below a threshold of 300, 250, 200,150, or 100 IU/mL, preferably below 300 IU/mL, and most preferably below a threshold of 150 IU/mL, and optionally, an eosinophil count in peripheral blood below 300 per µL, wherein the medicament is formulated at a dosage to allow subcutaneous delivery of at least about 75 mg-about 300 mg (e.g., about 75 mg, about 150 mg, about 300 mg, about 450 mg, about 600 mg), preferably about 75 mg-about 300 mg, of the IL-17 antagonist (e.g., IL-17 antibody or antigen-binding fragment thereof, e.g., secukinumab or CJM112) per unit dose, and further wherein the IL-17 antagonist (e.g., IL-17 antibody or antigen-binding fragment thereof, e.g., secukinumab or CJM112) binds to an epitope of an IL-17 homodimer having two mature IL-17 protein chains, said epitope comprising Leu74, Tyr85, His86, Met87, Asn88, Va1124, Thr125, Pro126, 11e127, Va1128, His129 on one chain and Tyr43, Tyr44, Arg46, Ala79, Asp80 on the other chain, wherein the IL-17 antibody or antigen-binding fragment thereof has a $K_D$ for human IL-17 of about 100-200 pM, and wherein the IL-17 antibody or antigen-binding fragment thereof has an in vivo half-life of about 4 weeks.

As used herein, the phrase "formulated at a dosage to allow [route of administration] delivery of [a designated dose]" is used to mean that a given pharmaceutical composition can be used to provide a desired dose of an IL-17 antagonist, e.g., an IL-17 antibody, e.g., secukinumab or CJM112, via a designated route of administration (e.g., SC or IV). As an example, if a desired subcutaneous dose is 300 mg, then a clinician may use 2 ml of an IL-17 antibody formulation having a concentration of 150 mg/ml, 1 ml of an IL-17 antibody formulation having a concentration of 300 mg/ml, 0.5 ml of an IL-17 antibody formulation having a concentration of 600 mg/ml, etc. In each such case, these IL-17 antibody formulations are at a concentration high enough to allow subcutaneous delivery of the IL-17 antibody. Subcutaneous delivery typically requires delivery of volumes of less than about 2 ml, preferably a volume of about 1 ml or less. Preferred formulations are liquid pharmaceutical compositions comprising: a) about 25 mg/mL to about 150 mg/mL secukinumab, about 10 mM to about 30 mM histidine pH 5.8, about 200 mM to about 225 mM trehalose, about 0.02% polysorbate 80, and about 2.5 mM to about 20 mM methionine; and b) about 150 mg/mL CJM112, 4.8 mM L-histidine, 15.2 mM L-histidine-HCl 220 mM sucrose and 0.04% polysorbate 20, at pH 6.0±0.5.

As used herein, the phrase "container having a sufficient amount of the IL-17 antagonist to allow delivery of [a designated dose]" is used to mean that a given container (e.g., vial, pen, syringe) has disposed therein a volume of an IL-17 antagonist (e.g., as part of a pharmaceutical composition) that can be used to provide a desired dose. As an example, if a desired dose is 150 mg, then a clinician may use 2 ml from a container that contains an IL-17 antibody formulation with a concentration of 75 mg/ml, 1 ml from a container that contains an IL-17 antibody formulation with a concentration of 150 mg/ml, 0.5 ml from a container contains an IL-17 antibody formulation with a concentration of 300 mg/ml, etc. In each such case, these containers have a sufficient amount of the IL-17 antagonist to allow delivery of the desired 150 mg dose.

In some embodiments of the disclosed uses, methods, and kits, the patient has moderate to severe inflammatory asthma.

In some embodiments of the disclosed uses, methods, and kits, the patient is monthly administered about 75 mg-about 600 mg (e.g., about 75 mg, about 150 mg, about 300 mg, about 450 mg, about 600 mg), preferably about 75 mg-about 300 mg, of the IL-17 antibody or antigen-binding fragment thereof (e.g., secukinumab or CJM112) by subcutaneous injection. In some embodiments of the disclosed uses, methods, and kits, the patient is monthly administered about 75 mg (e.g., 75 mg) of the IL-17 antibody or antigen-binding fragment thereof (e.g., secukinumab or CJM112) by subcutaneous injection. In some embodiments of the disclosed uses, methods, and kits, the patient is monthly administered about 300 mg (e.g., 300 mg) of the IL-17 antibody or antigen-binding fragment thereof (e.g., secukinumab or CJM112) by subcutaneous injection. In some embodiments of the disclosed uses, methods, and kits, the patient is given a single administration of about 150 mg-about 600 mg (e.g., about 150 mg, about 300 mg, about 450 mg, about 600 mg) of the IL-17 antibody or antigen-binding fragment thereof (e.g., secukinumab or CJM112) by subcutaneous injection.

In some embodiments of the disclosed uses, methods, and kits, the IL-17 antibody or antigen-binding fragment thereof comprises: i) an immunoglobulin heavy chain variable domain ($V_H$) comprising the amino acid sequence set forth as SEQ ID NO:30; ii) an immunoglobulin light chain variable domain ($V_L$) comprising the amino acid sequence set forth as SEQ ID NO:22; iii) an immunoglobulin $V_H$ domain comprising the amino acid sequence set forth as SEQ ID NO:30 and an immunoglobulin $V_L$ domain comprising the amino acid sequence set forth as SEQ ID NO:22; iv) an immunoglobulin $V_H$ domain comprising the hypervariable regions set forth as SEQ ID NO:24, SEQ ID NO:26, and SEQ ID NO:28; v) an immunoglobulin $V_L$ domain comprising the hypervariable regions set forth as SEQ ID NO:16, SEQ ID NO:18 and SEQ ID NO:20; vi) an immunoglobulin $V_H$ domain comprising the hypervariable regions set forth as SEQ ID NO:25, SEQ ID NO:27 and SEQ ID NO:29; vii) an immunoglobulin $V_L$ domain comprising the hypervariable regions set forth as SEQ ID NO:17, SEQ ID NO:19 and SEQ ID NO:21; viii) an immunoglobulin $V_H$ domain comprising the hypervariable regions set forth as SEQ ID NO:24, SEQ ID NO:26, and SEQ ID NO:28 and an immunoglobulin $V_L$ domain comprising the hypervariable regions set forth as SEQ ID NO:16, SEQ ID NO:18 and SEQ ID NO:20; ix) an immunoglobulin $V_H$ domain comprising the hypervariable regions set forth as SEQ ID NO:25, SEQ ID NO:27, and SEQ ID NO:29 and an immunoglobulin $V_L$ domain comprising the hypervariable regions set forth as SEQ ID NO:17, SEQ ID NO:19 and SEQ ID NO:21; x) a light chain comprising SEQ ID NO:23; xi) a heavy chain comprising SEQ ID NO:31; or xii) a light chain comprising SEQ ID NO:23 and a heavy chain comprising SEQ ID NO:31. In some embodiments of the disclosed uses, methods, and kits, the IL-17 antibody or antigen-binding fragment thereof is CJM112.

In some embodiments of the disclosed uses, methods, and kits, the IL-17 antibody or antigen-binding fragment thereof comprises: i) an immunoglobulin heavy chain variable domain ($V_H$) comprising the amino acid sequence set forth as SEQ ID NO:8; ii) an immunoglobulin light chain variable domain ($V_L$) comprising the amino acid sequence set forth as SEQ ID NO:10; iii) an immunoglobulin $V_H$ domain comprising the amino acid sequence set forth as SEQ ID NO:8 and an immunoglobulin $V_L$ domain comprising the amino acid sequence set forth as SEQ ID NO:10; iv) an immunoglobulin $V_H$ domain comprising the hypervariable regions set forth as SEQ ID NO:1, SEQ ID NO:2, and SEQ ID NO:3; v) an immunoglobulin $V_L$ domain comprising the hypervariable regions set forth as SEQ ID NO:4, SEQ ID NO:5 and SEQ ID NO:6; vi) an immunoglobulin $V_H$ domain comprising the hypervariable regions set forth as SEQ ID NO:11, SEQ ID NO:12 and SEQ ID NO:13; vii) an immunoglobulin $V_H$ domain comprising the hypervariable regions set forth as SEQ ID NO:1, SEQ ID NO:2, and SEQ ID NO:3 and an immunoglobulin $V_L$ domain comprising the hypervariable regions set forth as SEQ ID NO:4, SEQ ID NO:5 and SEQ ID NO:6; viii) an immunoglobulin $V_H$ domain comprising the hypervariable regions set forth as SEQ ID NO:11, SEQ ID NO:12 and SEQ ID NO:13 and an immunoglobulin $V_L$ domain comprising the hypervariable regions set forth as SEQ ID NO:4, SEQ ID NO:5 and SEQ ID NO:6; ix) an immunoglobulin light chain comprising the amino acid sequence set forth as SEQ ID NO:14; x) an immunoglobulin heavy chain comprising the amino acid sequence set forth as SEQ ID NO:15; or xi) an immunoglobulin light chain comprising the amino acid sequence set forth as SEQ ID NO:14 and an immunoglobulin heavy chain comprising the amino acid sequence set forth as SEQ ID NO:15. In some embodiments of the disclosed uses, methods, and kits, the IL-17 antibody or antigen-binding fragment thereof is secukinumab.

Disclosed herein are also methods of treating a patient having moderate to severe inflammatory asthma, comprising monthly administering the patient about 150 mg-about 600 mg of CJM112 by subcutaneous injection.

Kits and Devices

The disclosure also encompasses kits for treating asthma, e.g., moderate to severe asthma. Such kits comprise an IL-17 antagonist, e.g., IL-17 binding molecule (e.g., IL-17 antibody or antigen-binding fragment thereof, e.g., secukinumab or CJM112, or IL-17 receptor binding molecule (e.g., IL-17 antibody or antigen-binding fragment thereof) (e.g., in liquid or lyophilized form) or a pharmaceutical composition comprising the IL-17 antagonist (described supra). Additionally, such kits may comprise means for administering the IL-17 antagonist (e.g., an autoinjector, a syringe and vial, a prefilled syringe, a prefilled pen) and instructions for use. These kits may contain additional therapeutic agents (described supra) for treating asthma, e.g., for delivery in combination with the enclosed IL-17 antagonist, e.g., IL-17 binding molecule, e.g., IL-17 antibody, e.g., secukinumab or CJM112. Such kits may also comprise instructions for administration of the IL-17 antagonist (e.g., IL-17 antibody, e.g., secukinumab or CJM112) to treat asthma, e.g., moderate to severe asthma. Such instructions may provide the dose (e.g., 10 mg/kg, 75 mg, 150 mg, 300 mg, 450 mg, 600 mg), route of administration (e.g., IV, SC), and dosing regimen (e.g., monthly with or without an induction regimen) for use with the enclosed IL-17 antagonist, e.g., IL-17 binding molecule, e.g., IL-17 antibody, e.g., secukinumab or CJM112.

The phrase "means for administering" is used to indicate any available implement for systemically administering a drug to a patient, including, but not limited to, a pre-filled syringe, a vial and syringe, an injection pen, an autoinjector, an IV drip and bag, a pump, etc. With such items, a patient may self-administer the drug (i.e., administer the drug without the assistance of a physician) or a medical practitioner may administer the drug.

The phrase "therapeutically effective amount" is used to indicate a quantity of drug that can achieve a given stated effect, e.g., treatment of asthma.

Disclosed herein are kits for use in treating a patient having asthma, e.g., moderate to severe asthma, wherein the patient is to be selected based on having a total serum concentration of IgE below a threshold of 300, 250, 200,150, or 100 IU/mL, preferably below 300 IU/mL, and most preferably below a threshold of 150 IU/mL, and optionally, an eosinophil count in peripheral blood below 300 per µL, comprising an IL-17 antagonist (e.g., IL-17 binding molecule, e.g., IL-17 antibody or antigen-binding fragment thereof, e.g., secukinumab or CJM112. In some embodiments, the kit further comprises means for administering the IL-17 antagonist to the patient. In some embodiments, the kit further comprises instructions for administration of the IL-17 antagonist, wherein the instructions indicate that the IL-17 antagonist (e.g., IL-17 binding molecule, e.g., IL-17 antibody or antigen-binding fragment thereof, e.g., secukinumab or CJM112, is to be administered to the patient SC with or without a loading regimen, e.g., at about 75 mg-about 600 mg (e.g., about 75 mg, about 150 mg, about 300 mg, about 450 mg, about 600 mg) every 4 weeks (monthly). In some embodiments, the kit further comprises instructions for administration of the IL-17 antagonist, wherein the instructions indicate that the IL-17 antagonist (e.g., IL-17 binding molecule, e.g., IL-17 antibody or antigen-binding fragment thereof, e.g., secukinumab or CJM112, is to be administered a single time (once) to the patient SC with or without a loading regimen, e.g., at about 150 mg-about 600 mg (e.g., about 150 mg, about 300 mg, about 450 mg, about 600 mg). In some embodiments, the instructions will provide for dose escalation or dose reduction as needed, to be determined by a physician.

General

In preferred embodiments of the disclosed methods, treatments, medicaments, regimens, uses and kits, the IL-17 antagonist is an IL-17 binding molecule. In preferred embodiments, the IL-17 binding molecule is an IL-17 antibody or antigen-binding fragment thereof. In preferred embodiments of the disclosed methods, treatments, regimens, uses and kits, the IL-17 antibody or antigen-binding fragment thereof is a human antibody of the IgG$_1$ isotype. In preferred embodiments of the disclosed methods, the antibody or antigen-binding fragment thereof is secukinumab or CJM112.

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference. The following Examples are presented in order to more fully illustrate the preferred embodiments of the disclosure. These examples should in no way be construed as limiting the scope of the disclosed patient matter, as defined by the appended claims.

Methods for measuring total IgE as mentioned in Salkie, 1994 can be used. These include single radial immunodiffusion (SRID), nephelometry, radioimmunoassay (RIA), immunoradiometric assay (IRMA), enzyme immunoassay (EIA), fluoroimmunoassay (FIA), luminescent immunoassay (LIA).

In one specific embodiment, disclosed in Plebani (2003), a sandwich immunoassay might be used. Any antibody specific for IgE can be used in the sandwich immunoassay, and it can be labeled with a dye molecule, a gold particle, a colored-polymer particle, a fluorescent molecule, an enzyme, a red blood cell, a hemoglobin molecule, a magnetic particle or a carbon particle.

In one preferred embodiment, the system Niji™ total IgE test is used to assay the level of IgE. Niji™ Total IgE assay uses a sensitive pyro-electric sensor disclosed in WO2004/090512, hereby incorporated by reference in its entirety, to measure the amount of Total IgE in whole blood, as disclosed in WO2016/188902, hereby incorporated by reference in its entirety. As material binds to the sensor surface, the reporter is illuminated with light. This light is converted to heat which is measured by the pyro-electric sensor and is proportional to the amount of analyte present in the sample.

The Niji™ System, consists of a small desk-top analyzer, optional accessories, and test-specific disposable cartridges. It is based on a proprietary pyro-electric technology that supports the design of sensitive, rapid immunoassay tests using unprocessed capillary blood specimens. This allows the development of tests which quantitate proteins, antibodies, drug molecules and metabolites in capillary blood and other body fluids within 10 to 15 minutes.

The total IgE test is a sandwich immunoassay, utilizing an antibody specific for IgE, which is labeled with a carbon particle.

Example 1: Post Hoc Analysis of Severe Asthmatic Patients Treated with Anti-IL-17A (AIN457) Identified a Distinct Responder Population Asthma stratification efforts have predominantly focused on subgroups defined by levels of circulating and sputum eosinophils. In a recent study of anti-IL-17A treated severe asthma patients, post hoc unbiased analysis found that patients who responded to anti-IL-17A (i.e., >5% improvement in percent of predicted FEV1) had significantly lower levels of IgE (<150/ul) than non-responders. Response to anti-IL-17A intervention was not associated with a specific eosinophil cut-off level.

1. Study Design

A study was conducted under clinicaltrials.gov identifier CAIN457D2204. This was a multicenter, double-blind, randomized, placebo-controlled study in subjects with severe asthma (GINA step 4/5) that were not adequately controlled despite treatment with high doses of inhaled and/or oral corticosteroids and long-acting beta agonists. The study consisted of a screening period of 28-days, a 28-day run-in period, and a baseline assessment. This was followed by exposure to anti-IL-17A (AIN457; secukinumab; 10 mg/kg), as compared to placebo at days 15, 29 and 57. Primary analysis was performed at Day 85 assessing percent of predicted FEV1 and ACQ. Patients were randomized 2:1 (30 treated, 15 placebo).

The study design is presented in FIG. 1.

2. Exploratory Biomarker Assessments

Biomarkers were assessed by an integrated molecular approach examining genetics, mRNA/miRNA expression in Peripheral Blood Mononuclear Cells (PBMC's), and nasal epithelial cells, plasma miRNA, and protein profiling.

3. Methods

PBMC and nasal brushings samples were collected at multiple timepoints throughout the course of the study. Transcriptomics data were generated using Affymetrix arrays. Data were analysed using Linear Models for Microarray and RNA-Seq Data (LIMMA) R package. The lists of differentially expressed genes were further interrogated using pathway analysis toolkit from Clarivate Analytics (MetaCore and Lung disease module).

4. Results

Responders were defined as >5% change from baseline of percent predicted FEV1. A summary of the results is shown in Table 3.

TABLE 3

Summary of results

| Compound | Secukinumab (n = 29) |
|---|---|
| Efficacy Criteria | FEV1PCHG (>=5) |
| Number of responders | 13 |
| Number of non-responders | 16 |
| Average FEV1PCHG (In Resp vs. Non-resp) | 13.5 vs. −6.16 |
| Average IgE (In Resp vs. Non-resp) | 49.08 vs. 199.23 |
| Average EoS (In Resp vs. Non-resp) | 180 vs. 210 |

Post hoc analysis of the AIN457 responder subgroup was aimed at characterizing the responders clinically as well as molecularly, utilizing the exploratory profiling data. Analysis of available clinical endpoints revealed that total IgE levels in the responder subgroup were significantly lower than that of the non-responder subgroup.

IgE stood out as a discriminating factor with a p-value of 0.01, as determined by the Student T-Test comparing means of responder/non-responder subgroups.

On a molecular level, nasal brushings and PBMC transcriptomics were used to characterize responders and non-responders at baseline.

In nasal brushings, 154 differentially regulated genes were identified, and pathway analysis of the differentially regulated genes identified a number of asthma related pathways. The top two enriched pathways, both upregulated in responders, were "Neutrophil chemotaxis in asthma" and "Release of pro-inflammatory factors and proteases by alveolar macrophages in asthma". In PBMC, 22 genes were differentially regulated, including genes involved in the pathway "IgE-dependent production of pro-inflammatory mediators by neutrophils in asthma", which was downregulated in responders.

5. Conclusions

Unbiased analysis determined that severe asthma responders to anti-IL-17A were those patients with IgE<150/uL, and markers of increased nasal epithelial neutrophilic inflammation, while markers of systemic inflammation, especially IgE driven, were decreased.

The data suggest that, at baseline, anti-IL-17A responders and non-responders appear to be molecularly distinct. The conclusion is supported by the total IgE differences, described above.

Example 2: Clinical Study to Assess the Efficacy and Safety of CJM112 in Patients with Inadequately Controlled Moderate to Severe Asthma The purpose of this study is to determine whether CJM112, when added to existing therapy, displays the clinical efficacy and safety profile to support further development in patients with inadequately controlled moderate to severe asthma.

CJM112 cross-reacts with cynomolgus monkey and rat IL-17A, therefore, these species were selected for toxicological evaluation. In vitro blood compatibility analysis as well as in vivo safety pharmacology investigations, including neurobehavioral (functional observation tests), respiratory (blood gas analysis) and telemetric cardiovascular electrocardiogram (ECG) and blood pressure, were performed in the 13 week cynomolgus monkey study, and did not show any adverse reactions (data not shown). No non-specific tissue cross-reactivity was demonstrated when CJM112 was applied to normal human, cynomolgus monkey or rat tissues (data not shown).

CJM112 administered intravenously (i.v.) or subcutaneously (s.c.) to cynomolgus monkeys (once weekly for 13 weeks) and rats (once weekly for up to 26 weeks), was well tolerated and did not show any significant toxicological or local tolerability effects. No infections or hypersensitivity reactions were observed in any of the animals (data not shown).

Clinical development of CJM112 was initiated in a first-in-human (FIH) study in patients with chronic plaque type psoriasis (CCJM112X2101, data not shown). Three additional clinical trials with CJM112 (hidradenitis suppurativa, acne and metastatic tumors) are currently on-going (data not shown).

1. Study Design

To investigate the usefulness of IL-17 antagonists, preferably CJM112, to treat patients with inadequately controlled moderate to severe asthma, the following non-confirmatory, randomized, subject- and investigator-blinded, placebo-controlled, multi-center, parallel-arm study evaluating the efficacy of CJM112 on top of standard of care in patients with inadequately controlled moderate to severe asthma is conducted.

The study will enroll approximately 110 patients. After an initial screening visit and run-in period of 4 weeks, subjects eligible per inclusion and exclusion criteria at the baseline visit will be randomized (3:2) to receive 9 doses of 300 mg of CJM112 or matching placebo sub-cutaneously over 3 months at the clinical study site. All baseline safety evaluation results must be available prior to dosing. After the end of the treatment period, subjects will be followed for an additional 13 weeks. Out-patient visits to administer dose and assess safety and efficacy will be scheduled as depicted in the figure below. Safety assessments will include physical examinations, ECGs, vital signs, standard clinical laboratory evaluations (hematology, blood chemistry, and urinalysis), adverse event and serious adverse event monitoring.

Figure 2:
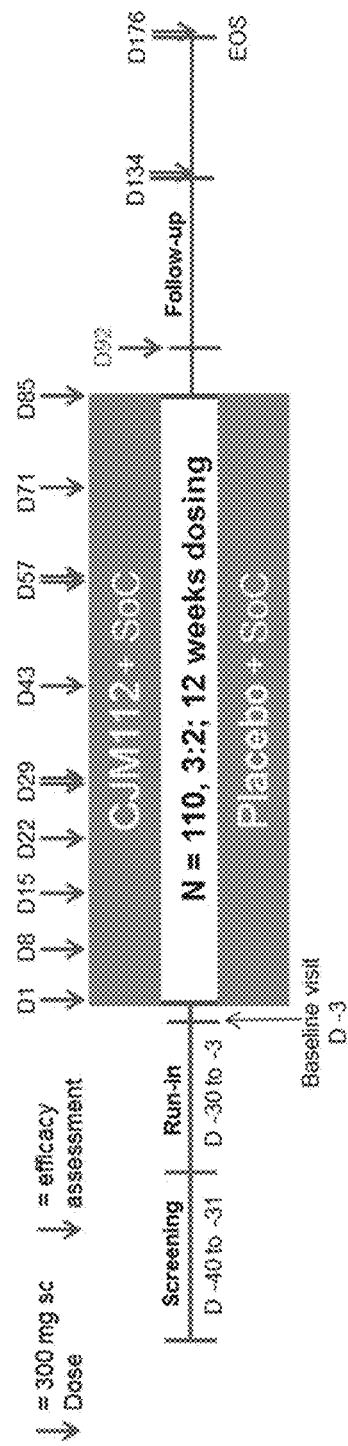
FIG. 2 is a schematic representation of a study design.

The study design is presented in FIG. 2 and set forth below.

Screening and Run-In: After providing informed consent and an initial screening visit on Day −31 consisting of vital signs, physical exam, blood chemistry, ECG, pulmonary function tests, and ACQ7. Subjects who meet all eligibility criteria at the screening visit will perform a daily diary including peak flow measurements and daily symptoms over 28 days until the baseline visit. This 28-day period is referred to as run-in.

Baseline: Subjects who qualify based on screening and run-in assessments will return for a baseline evaluation on Day −3. Subjects who meet all the applicable inclusion/exclusion criteria at screening and baseline will be randomized and will enter the treatment period. All screening and baseline assessments results must be available prior to randomization.

Treatment Period: On Day 1 of the treatment period, after completion of all pre-dose assessments, subjects will receive a single dose of CJM112 or placebo for each week for the first 29 days (4 weeks). After Day 29, subjects will receive a single dose of CJM112 or placebo every two weeks up to, and including, day 85 (week 12).

At treatment period visits, safety, PK and PD assessments will be performed. Safety assessments will include physical examinations, systems review, open ended health inquiry, ECGs, vital signs, standard clinical laboratory evaluations (hematology, blood chemistry, urinalysis), AEs and SAE monitoring.

Subjects will complete dosing on Day 85 and will return for final efficacy assessment a week later on Day 92 to complete an End of Treatment (EOT) period visit.

Subjects who discontinue treatment early (unless they have withdrawn consent) should complete the Day 92, Follow-up, and EOS visit. If a subject withdraws consent, then the EOS visit should be completed.

Safety Follow-up: After completing the day 92 visit, subjects will enter a 13-week follow-up period consisting of a visit on Day 134 and an End of Study (EOS) visit on Day 176.

Patients with asthma in this study will continue the standard of care medications as prescribed by their primary physicians. Hence the study design includes a placebo control and not an active control because the study treatment will be added on top of standard of care. The placebo arm is expected to control for potential bias in efficacy and safety assessments in the study.

Patients eligible to participate in this study will be required to demonstrate symptoms of un-controlled asthma (as defined by an Asthma Control Questionnaire score of at least 1.5) despite compliance with standard of care therapy for moderate or severe asthma according to local practice. Thus the background therapy will include at least medium dose inhaled glucocorticoids and at least one additional asthma controller medication.

2. Study Objectives

The primary objective of the study is to determine whether treatment with CJM112 in patients with inadequately controlled moderate to severe asthma leads to an improvement in airflow obstruction. The primary objective is measured by change from baseline as determined by the lung function test forced expiratory volume 1 (FEV1) in mL, described in Miller et al. (2006).

The study also has the following secondary objectives.

To determine whether treatment with CJM112 in patients with inadequately controlled moderate to severe asthma leads to an improvement in FEV1% of predicted, as measured by Change from baseline FEV1% of predicted.

To determine whether treatment with CJM112 in patients with inadequately controlled moderate to severe asthma leads to an improvement in asthma control, as measured by Change from baseline as determined by asthma control questionnaire (ACQ) score, % of patients with 0.5 decrease in ACQ score.

To assess the safety and tolerability of CJM112 in patients with inadequately controlled moderate to severe asthma, as measured by absence of adverse events.

3. Rationale for the Study Design

This study is an exploratory, multi-center, randomized, double-blind, parallel-group, phase IIa study with a 12 week treatment epoch. Participants will receive 9 doses of CJM112 or placebo s.c. over 12 weeks. The last dose will be administered on study day 85 and key efficacy will be evaluated one week thereafter on study day 92.

An unmet medical need exists for patient with moderate and severe asthma who continue to demonstrate symptoms despite being on standard of care medications, and are not eligible for other biologic therapies developed or in development for T2-high (allergic/eosinophilic) asthma (such as omalizumab, mepolizumab, reslizumab, dupilumab) because they have low circulating IgE and eosinophil levels at baseline.

In order to optimize the rigor and integrity of the study and minimize bias, a randomized, subject- and investigator-blinded parallel group study design is used. This design is well-established in respiratory clinical trials and enables the study treatment to be given for an appropriate and practical length of time to assess the efficacy and safety of the treatment.

The placebo arm controls for potential bias in efficacy and safety assessments. The study design includes a placebo control and not an active control because the study treatment will be added on top of standard of care.

To ensure subject's eligibility for the study at the baseline visit after their standard of care treatment has been adhered to post-screening, and minimize the potential for changes in key endpoints as a result of regression to the mean at the end of the study period.

The terminal half-life of CJM112 is currently estimated to be 18 days based on available clinical data from psoriasis patients. Hence, a 13-week follow up period is proposed after the last dose on study day 85 to ensure patient safety, compliance with contraception requirements, and to assess for loss of efficacy after 5 half-lives of the investigational treatment.

4. Rationale of Dose/Regimen, Duration of Treatment

The study participants will receive CJM112 300 mg or placebo sc injections 9 times during the 12 week treatment period: 5 weekly doses of 300 mg sc each (induction/loading) and 4 subsequent doses every 2 weeks (maintenance). This regimen is considered as practical and feasible for this severe asthma population. A weekly loading dose regimen of 5 doses of 300 mg has been safe and well-tolerated in patients with hidradenitis suppurativa and is justified to reach close to steady state conditions in PK after the first month. The 12 week treatment duration is considered adequate to demonstrate improvements in the key endpoints in patients with severe asthma based on published literature (Wenzel et al. 2016), the known pharmacokinetic properties of CJM112 from ongoing studies, and known pharmacodynamic properties of secukinumab in patients with asthma (data not shown).

The available pre-clinical package includes two 13-week toxicological studies in cynomolgus monkeys and rats up to 150 mg/kg/week i.v. or s.c., as well as a 26-week study in rats (up to 150 mg/kg/week i.v. or s.c.), with no adverse effect including the immune function. This package is considered adequate for the proposed dose and duration of treatment regimen in this study.

In humans, CJM112 has been studied in a single ascending dose study up to 450 mg (psoriasis patients). It has been studied in multiple doses in adults with psoriasis (up to 150 mg s.c. every week for a month and then every 2 weeks; cumulative dose of 1350 mg over 12 weeks) and is currently being studied in hidradenitis suppurativa in a more frequent dosing schedule (300 mg s.c. every week for a month and then every 2 weeks; cumulative dose of 3000 mg over 14 weeks) which is about the schedule we propose to use in this asthma study (cumulative dose of 2700 mg over 12 weeks). To date, no serious systemic safety signal has been detected.

5. Population

The study population will consist of approximately 110 male and female patients with uncontrolled symptoms of moderate or severe asthma (defined by ACQ score of 1.5) on standard of care medications. Drop-outs after randomization will not be replaced.

The investigator must ensure that all subjects being considered for the study meet the following eligibility criteria. No additional criteria should be applied by the investigator, in order that the study population will be representative of all eligible subjects.

Subject selection is to be established by checking through all applicable eligibility criteria at screening and baseline. A relevant record (e.g. checklist) of the eligibility criteria must be stored with the source documentation at the study site.

Deviation from any entry criterion excludes a subject from eligibility for the study.

1. Inclusion Criteria

The following criteria must be fulfilled by patients eligible for inclusion:
  i. Written informed consent must be obtained before any assessment is performed
  ii. Able to communicate well with the investigator, to understand and comply with the requirements of the study.
  iii. Male and female adult patients aged 18 to 75 years.
  iv. Patients must weigh between 50 and 120 kg
  v. Patients with a physician-diagnosed history of moderate to severe asthma (GINA 2015 step 4) for a period of at least one year prior to screening
  vi. Patients on a stable therapy regimen for asthma for at least 3 months prior to screening with at least medium dose inhaled glucocorticoids and at least one additional asthma controller medication (such as inhaled long-acting bronchodilator, leukotriene antagonist, theophylline, stable low dose glucocorticoid, etc)
  vii. Acceptable and reproducible spirometry with FEV1 40 and 90% of predicted at screening and baseline (Re-testing is allowed once)
  viii. ACQ score≥1.5 at screening and baseline (Re-testing is allowed once)
  ix. Total serum IgE<150 IU/mL
  x. Peripheral blood eosinophils<300/μL
  xi. ≥80% compliance with PEF and diary recording during the run-in period 2. Exclusion Criteria Patients fulfilling the following criteria are not eligible for inclusion:
  i. Use of investigational drugs at the time of screening, or within 4 weeks or 5 half-lives of screening, or as required by local regulations, whichever is longer.
  ii. Treatment with IL-17 or IL17R blocking agents over the previous 12 months, including, but not limited to secukinumab, ixekizumab, bimekizumab and brodalumab.
  iii. Previous use of biologics or other concomitant medications within time periods specified in the SOM/protocol.
  iv. Women of child-bearing potential, defined as all women physiologically capable of becoming pregnant, unless they are using highly effective methods of contraception during dosing and for 13 weeks after stopping of investigational drug. Highly effective contraception methods include:
    a. Total abstinence from heterosexual intercourse (when this is in line with the preferred and usual lifestyle of the subject). Periodic abstinence (e.g. calendar, ovulation, symptothermal, post-ovulation methods) and withdrawal are not acceptable methods of contraception.
    b. Female sterilization (have had surgical bilateral oophorectomy with or without hysterectomy), total hysterectomy or tubal ligation at least six weeks before taking investigational drug. In case of oophorectomy alone, only when the reproductive status of the woman has been confirmed by follow up hormone level assessment.
    c. Male sterilization (at least 6 months prior to screening). For female subjects in the study the vasectomized male partner should be the sole partner for that subject.
    d. Use of oral, injected or implanted hormonal methods of contraception or placement of an intrauterine device (IUD) or intrauterine system (IUS) or other forms of hormonal contraception that have comparable efficacy (failure rate <1%), for example hormone vaginal ring or transdermal hormone contraception In case of use of oral contraception, women should be stable on the same pill for a minimum of 3 months before taking investigational drug. Women are considered post-menopausal and not of child bearing potential if they have had 12 months of natural (spontaneous) amenorrhea with an appropriate clinical profile (e.g. age appropriate, history of vasomotor symptoms) or have had surgical bilateral oophorectomy (with or without hysterectomy), total hysterectomy or tubal ligation at least six weeks ago. In the case of oophorectomy alone, only when the reproductive status of the woman has been confirmed by follow up hormone level assessment is she considered not of child bearing potential.
  v. Pregnant or nursing (lactating) women, where pregnancy is defined as the state of a female after conception and until the termination of gestation, confirmed by a positive hCG laboratory test.
  vi. History of ongoing, chronic or recurrent infectious disease.
  vii. Patients with chronic lung diseases other than asthma, including (but not limited to) chronic obstructive pulmonary disease, clinically significant bronchiectasis, sarcoidosis, interstitial lung disease, cystic fibrosis, Churg-Strauss syndrome, allergic broncho-pulmonary aspergillosis, or clinically significant chronic lung diseases related to a history of tuberculosis or asbestosis.
  viii. History of severe systemic *Candida* infections or evidence of Candidiasis in the 2 weeks prior to baseline visit.
  ix. Active systemic infections during the 2 weeks prior to baseline.
  x. History of immunodeficiency diseases, including a positive HIV (ELISA and Western blot) test result at screening.
  xi. A positive Hepatitis B surface antigen or Hepatitis C test result at screening
  xii. Any live vaccines (this includes nasal-spray flu vaccine) starting from 6 weeks before baseline
  xiii. Any severe, progressive or uncontrolled, acute or chronic, medical or psychiatric condition, or other factors such as abnormal vital signs, ECG or physical findings, or clinically relevant abnormal laboratory values, that in the judgment of the investigator may increase the risk associated with study participation/treatment or may interfere with interpretation of study results, and thus would make the patient inappropriate for entry into or continuing the study.

xiv. History of hypersensitivity or allergy to the investigational compound/compound class being used in this study.

xv. Donation or loss of 400 ml or more of blood within 8 weeks prior to baseline, or longer if required by local regulation.

xvi. History of drug or alcohol abuse within the 12 months prior to dosing.

xvii. At screening, history or symptoms of malignancy of any organ system (except for a history of basal cell carcinomas and/or up to 3 squamous cell carcinomas of the skin, if successful treatment has been performed, with no signs of recurrence; actinic keratosis, if present at screening, should be treated according to standard therapy before randomization), treated or untreated, within the past 5 years, regardless of whether there is evidence of local recurrence or metastases.

xviii. Patients with known active Crohn's disease.

xix. Patients who have smoked or inhaled nicotine or tobacco products within the 6 month period prior to Visit 1, or who have a smoking history of greater than 10 pack years (e.g. 10 pack years=1 pack/day×10 years or % pack/day×20 years, etc.).

xx. History of life-threatening asthma event in the previous year, such as significant hypercarbia (pCO2>45 mmHg), endotracheal intubation, non-invasive positive pressure ventilation (NIPPV), respiratory arrest, or seizure as a result of asthma.

xxi. Patients who have had an asthma attack/exacerbation requiring systemic corticosteroids for at least 3 continuous days within 6 weeks prior to screening (re-screening is permitted).

xxii. Patients who have had a respiratory tract infection or asthma worsening within 4 weeks prior to Visit 1 (Screening) or during the screening period.

xxii. Patients may be re-screened 4 weeks after recovery from their respiratory tract infection or asthma worsening.

No additional exclusions may be applied, in order to ensure that the study population will be representative of all eligible patients.

Each concomitant drug must be individually assessed against all exclusion criteria and the table below to see if it is allowed. If in doubt, the investigator should contact the medical monitor before randomizing a patient or allowing a new medication to be started.

The following drugs are excluded to ensure patient safety and prevent confounding of efficacy in this clinical trial.

6. Treatment

Patients will receive treatment with either CJM112, formulated as liquid in vial, 150 mg/ml, 1 ml. Placebo is also liquid in vial, 1 ml, but without CJM112.

Subjects will be assigned to one of the following two treatment arms in a ratio of 3:2 Study treatments are defined as (FIG. 2):

CJM112: 5 weekly doses of 300 mg (2 vials) s.c. each and 4 subsequent 300 mg (2 vials) s.c. doses every 2 weeks. Total 9 doses over 12 weeks of 300 mg (2 vials) s.c. each.

Placebo to CJM112: 5 weekly doses of 0 mg (2 vials) s.c. each and 4 subsequent 0 mg (2 vials) s.c. doses every 2 weeks. Total 9 doses over 12 weeks of 0 mg (2 vials) s.c. each.

Study completion is defined as when the last subject completes their Study Completion visit, and any repeat assessments associated with this visit have been documented and followed-up appropriately by the Investigator, or in the event of an early study termination decision, the date of that decision.

All subjects should have the follow up visit and an end-of-study visit.

7. Analysis

Clinically relevant questionnaires that will be administered during the course of the study include two validated questionnaires (the Asthma Control Questionnaire or ACQ, and the Asthma Quality of Life Questionnaire or the AQLQ). These will be administered at various time points during the study.

Spirometry testing will be performed according to the American Thoracic Society guidelines at screening to assess patients' eligibility for the study and at repeated intervals.

A body plethysmograph will be used to measure Functional Residual Capacity (FRC), Inspiratory Capacity (IC), Total Lung Capacity (TLC), and Residual Volume (RV). All plethysmography evaluations should follow the recommendations of the ATS/ERS Task force: Standardization of the measurement of lung volumes (Wanger et al 2005).

The primary efficacy analysis will assess the effect of CJM112 on the absolute change from baseline in trough FEV1 in mL compared to placebo on Day 92.

A Bayesian linear repeated measures model will be used to analyze the absolute change from baseline in trough FEV1 up to EOS visit. The model will include fixed effects of treatment by visit baseline by visit. Visit will be treated as a categorical variable, and baseline FEV1 as a continuous covariate. An unstructured covariance matrix will be assumed for the repeated measures per individual patient. An informative prior will be used on the parameters for the placebo group on Day 92. This prior is obtained from a meta-analysis on the selected historical placebo population from six historical studies. Posterior inference such as the posterior probability of change from baseline in CJM112 group is larger than that in the placebo group will be obtained. The model will also be analyzed under the frequentist framework as a sensitivity analysis.

The secondary efficacy analyses will assess the effect of CJM112 on the absolute change from baseline in trough FEV1 in % of predicted and ACQ scores compared to placebo, with the primary interest on Day 92 of the study.

8. Sample Size Calcination

Approximately, a hundred and ten patients are planned to be randomized in a 3:2 ratio to receive CJM112 vs. placebo, with the intent that at least 100 patients will complete the study, allowing for 10% drop-out rate.

The sample size calculation is based on the primary endpoint of change from baseline in FEV1 on Day 92. The criterion for this calculation aims for a 90% level of proof that the change from baseline of FEV1 in the CJM112 group is larger than that in the placebo group.

To derive a prior distribution for the change from baseline in the placebo group, we conducted a meta-analysis on the change from baseline of FEV1 at week 12 for the placebo groups of 392 total subjects from six selected historical clinical trials. From this analysis, we conclude that the prior distribution for the change from baseline in FEV1 at Week 12 in the placebo group is a normal distribution with mean 49 ml and standard deviation 52 ml which corresponds to approximately 21 subjects for the placebo group. This prior is used as the informative prior for the placebo group at Day 92, with the assumption that the placebo group at Day 92 behaves similarly to Week 12 (Day 85).

At Day 92, with a non-informative prior for the CJM112 group, and the obtained informative prior for the placebo group, a sample size of 100 (3:2 ratio of CJM112:placebo) provides approximately 83% chance (power) of meeting the success criterion, assuming the effect size is 100 ml and the SD is 260ml; and approximately 8% change of falsely meeting the success criterion when CJM112 is placebo-like and has no beneficial effect. With this sample size, the probability of stopping early for futility is approximately 40% in case of a placebo-like drug and less than 3% in case the true treatment effect is 100 ml. 100 ml is considered the minimum clinically significant difference between drug and placebo in this severe asthma patient population.

9. Interim Analysis

At least two unblinded interim analyses (IA) are planned during the trial. The first unblinded IA will be conducted after approximately 35 randomized subjects complete the study Day 92 visit. The purpose of this IA is to confirm the sample size assumptions and assess safety. In the situation where sample size increasement is needed, the adjusted sample size will not exceed 200. The study will not be stopped for futility or early success at this IA. The second unblinded IA will be conducted after approximately 70 randomized subjects complete the study Day 92 visit. The purpose of this IA is to evaluate safety, efficacy and futility. The study may be stopped for futility if there is less than 40% posterior probability that the effect of CJM112 on change from baseline in FEV1 is better than placebo.

Potential study design adaptations/modifications may be made based on interim results (e.g. for changes in dose, randomization ratio, duration of treatment or follow-up, sample size, endpoints, population).

Additional interim analyses may be conducted to support decision making concerning the current clinical study, the sponsor's clinical development projects in general or in case of any safety concerns.

REFERENCES

Bullens D M, Truyen E, Coteur L, et al. (2006) IL-17 mRNA in sputum of asthmatic patients: linking T cell driven inflammation and granulocytic influx? Respir. Res. p. 135.

Busse W W, Holgate S, Kerwin E, et al. (2013) Randomized, double-blind, placebo-controlled study of brodalumab, a human anti-IL-17 receptor monoclonal antibody, in moderate to severe asthma. Am. J. Respir. Crit. Care Med. p. 1294-302.

Chung K F, Wenzel S E, Brozek J L, et al. (2014) International ERS/ATS guidelines on definition, evaluation and treatment of severe asthma. Eur. Respir. J. p. 343-73.

Cosmi L, Liotta F, Maggi E, et al. (2011) Th17 cells: new players in asthma pathogenesis. Allergy p. 989-98.

McGrath K W, Icitovic N, Boushey H A, et al. (2012) A large subgroup of mild-to-moderate asthma is persistently noneosinophilic. Am. J. Respir. Crit. Care Med. p. 612-9.

Miller M R, et al. (2005) Standardisation of spirometry. Eur. Respir. J. 26:319-338.

Plebani M (2003) Clinical value and measurement of specific IgE. Clinical Biochemistry p. 453-469.

Thomson N C (2016) Novel approaches to the management of noneosinophilic asthma. Ther Adv Respir Dis p. 211-34.

Salkie M L (1994) Role of clinical laboratory in allergy testing. Clinical Biochemistry, p. 343-355.

Seagroatt V, Anderson S G (1981) The second international reference preparation for human serum immunoglobulin E and the first British standard for human serum immunoglobulin E. J. Biol Stand p. 431-437.

Wagner, J, et al. (2005) Standardization of the measurement of lung volumes. The European respiratory journal, p. 511-22.

Wenzel S, Castro M, Corren J, et al. (2016) Dupilumab efficacy and safety in adults with uncontrolled persistent asthma despite use of medium-to-high-dose inhaled corticosteroids plus a long-acting β2 agonist: a randomised double-blind placebo-controlled pivotal phase 2b dose-ranging trial. Lancet p. 31-44.

Woodruff P G, Modrek B, Choy D F, et al. (2009) T-helper type 2-driven inflammation defines major subphenotypes of asthma. Am. J. Respir. Crit. Care Med. p. 388-95.

Sequence Table

Useful amino acid and nucleotide sequences for practicing the invention are disclosed in Table 4.

TABLE 4

Sequences according to embodiments of the invention

| SEQ ID NUMBER | Ab region | Sequence |
|---|---|---|
| Secukinumab | | |
| SEQ ID NO: 1 (Kabat) | HCDR1 | NYWMN |
| SEQ ID NO: 2 (Kabat) | HCDR2 | AINQDGSEKYYVGSVKG |
| SEQ ID NO: 3 (Kabat) | HCDR3 | DYYDILTDYYIHYWYFDL |
| SEQ ID NO: 11 (Chothia) | HCDR1 | GFTFSNYWMN |
| SEQ ID NO: 12 (Chothia) | HCDR2 | AINQDGSEKYY |
| SEQ ID NO: 13 (Chothia) | HCDR3 | CVRDYYDILTDYYIHYWYFDLWG |
| SEQ ID NO: 8 | VH | EVQLVESGGGLVQPGGSLRLSCAASGFTFSNYWMNWVRQAPGKGLEWVAAINQDGSEKYYVGSVKGRFTISRDNAKNSLYLQMNSLRVEDTAVYYCVRDYYDILTDYYIHYWYFDLWGRGTLVTVSS |

TABLE 4-continued

Sequences according to embodiments of the invention

| SEQ ID NUMBER | Ab region | Sequence |
|---|---|---|
| SEQ ID NO: 7 | DNA VH | GAGGTGCAGTTGGTGGAGTCTGGGGGAGG<br>CTTGGTCCAGCCTGGGGGGTCCCTGAGACT<br>CTCCTGTGCAGCCTCTGGATTCACCTTTAGT<br>AACTATTGGATGAACTGGGTCCGCCAGGCT<br>CCAGGGAAAGGGCTGGAGTGGGTGGCCGC<br>CATAAACCAAGATGGAAGTGAGAAATACTAT<br>GTGGGCTCTGTGAAGGGCCGATTCACCATC<br>TCCAGAGACAACGCCAAGAACTCACTGTAT<br>CTGCAAATGAACAGCCTGAGAGTCGAGGAC<br>ACGGCTGTGTATTACTGTGTGAGGGACTATT<br>ACGATATTTTGACCGATTATTACATCCACTAT<br>TGGTACTTCGATCTCTGGGGCCGTGGCACC<br>CTGGTCACTGTCTCCTCA |
| SEQ ID NO: 15 | Heavy Chain | EVQLVESGGGLVQPGGSLRLSCAASGFTFSN<br>YWMNWVRQAPGKGLEWVAAINQDGSEKYYV<br>GSVKGRFTISRDNAKNSLYLQMNSLRVEDTAV<br>YYCVRDYYDILTDYYIHYWYFDLWGRGTLVTV<br>SSASTKGPSVFPLAPSSKSTSGGTAALGCLVK<br>DYFPEPVTVSWNSGALTSGVHTFPAVLQSSG<br>LYSLSSVVTVPSSSLGTQTYICNVNHKPSNTK<br>VDKRVEPKSCDKTHTCPPCP |
| SEQ ID NO: 32 | DNA Heavy Chain | GAGGTGCAGTTGGTGGAGTCTGGGGGAGG<br>CTTGGTCCAGCCTGGGGGGTCCCTGAGACT<br>CTCCTGTGCAGCCTCTGGATTCACCTTTAGT<br>AACTATTGGATGAACTGGGTCCGCCAGGCT<br>CCAGGGAAAGGGCTGGAGTGGGTGGCCGC<br>CATAAACCAAGATGGAAGTGAGAAATACTAT<br>GTGGGCTCTGTGAAGGGCCGATTCACCATC<br>TCCAGAGACAACGCCAAGAACTCACTGTAT<br>CTGCAAATGAACAGCCTGAGAGTCGAGGAC<br>ACGGCTGTGTATTACTGTGTGAGGGACTATT<br>ACGATATTTTGACCGATTATTACATCCACTAT<br>TGGTACTTCGATCTCTGGGGCCGTGGCACC<br>CTGGTCACTGTCTCCTCAGCCTCCACCAAG<br>GGCCCATCGGTCTTCCCCCTGGCACCCTCC<br>TCCAAGAGCACCTCTGGGGGCACAGCGGC<br>CCTGGGCTGCCTGGTCAAGGACTACTTCCC<br>CGAACCGGTGACGGTGTCGTGGAACTCAGG<br>CGCCCTGACCAGCGGCGTGCACACCTTCCC<br>GGCTGTCCTACAGTCCTCAGGACTCTACTC<br>CCTCAGCAGCGTGGTGACCGTGCCCTCCAG<br>CAGCTTGGGCACCCAGACCTACATCTGCAA<br>CGTGAATCACAAGCCCAGCAACACCAAGGT<br>GGACAAGAGAGTTGAGCCCAAATCTTGTGA<br>CAAAACTCACACATGCCCACCGTGCCCATA<br>A |
| SEQ ID NO: 4 (Kabat) | LCDR1 | RASQSVSSSYLA |
| SEQ ID NO: 5 (Kabat) | LCDR2 | GASSRAT |
| SEQ ID NO: 6 (Kabat) | LCDR3 | QQYGSSPCT |
| SEQ ID NO: 4 (Chothia) | LCDR1 | RASQSVSSSYLA |
| SEQ ID NO: 5 (Chothia) | LCDR2 | GASSRAT |
| SEQ ID NO: 6 (Chothia) | LCDR3 | QQYGSSPCT |
| SEQ ID NO: 10 | VL | EIVLTQSPGTLSLSPGERATLSCRASQSVSSS<br>YLAWYQQKPGQAPRLLIYGASSRATGIPDRFS<br>GSGSGTDFTLTISRLEPEDFAVYYCQQYGSSP<br>CTFGQGTRLEIKR |

TABLE 4-continued

Sequences according to embodiments of the invention

| SEQ ID NUMBER | Ab region | Sequence |
| --- | --- | --- |
| SEQ ID NO: 9 | DNA VL | GAAATTGTGTTGACGCAGTCTCCAGGCACC<br>CTGTCTTTGTCTCCAGGGGAAAGAGCCACC<br>CTCTCCTGCAGGGCCAGTCAGAGTGTTAGC<br>AGCAGCTACTTAGCCTGGTACCAGCAGAAA<br>CCTGGCCAGGCTCCCAGGCTCCTCATCTAT<br>GGTGCATCCAGCAGGGCCACTGGCATCCCA<br>GACAGGTTCAGTGGCAGTGGGTCTGGGACA<br>GACTTCACTCTCACCATCAGCAGACTGGAG<br>CCTGAAGATTTTGCAGTGTATTACTGTCAGC<br>AGTATGGTAGCTCACCGTGCACCTTCGGCC<br>AAGGGACACGACTGGAGATTAAACGA |
| SEQ ID NO: 14 | Light Chain | EIVLTQSPGTLSLSPGERATLSCRASQSVSSS<br>YLAWYQQKPGQAPRLLIYGASSRATGIPDRFS<br>GSGSGTDFTLTISRLEPEDFAVYYCQQYGSSP<br>CTFGQGTRLEIKRTVAAPSVFIFPPSDEQLKSG<br>TASVVCLLNNFYPREAKVQWKVDNALQSGNS<br>QESVTEQDSKDSTYSLSSTLTLSKADYEKHKV<br>YACEVTHQGLSSPVTKSFNRGEC |
| SEQ ID NO: 33 | DNA Light Chain | GAAATTGTGTTGACGCAGTCTCCAGGCACC<br>CTGTCTTTGTCTCCAGGGGAAAGAGCCACC<br>CTCTCCTGCAGGGCCAGTCAGAGTGTTAGC<br>AGCAGCTACTTAGCCTGGTACCAGCAGAAA<br>CCTGGCCAGGCTCCCAGGCTCCTCATCTAT<br>GGTGCATCCAGCAGGGCCACTGGCATCCCA<br>GACAGGTTCAGTGGCAGTGGGTCTGGGACA<br>GACTTCACTCTCACCATCAGCAGACTGGAG<br>CCTGAAGATTTTGCAGTGTATTACTGTCAGC<br>AGTATGGTAGCTCACCGTGCACCTTCGGCC<br>AAGGGACACGACTGGAGATTAAACGAACTG<br>TGGCTGCACCATCTGTCTTCATCTTCCCGCC<br>ATCTGATGAGCAGTTGAAATCTGGAACTGCC<br>TCTGTTGTGTGCCTGCTGAATAACTTCTATC<br>CCAGAGAGGCCAAAGTACAGTGGAAGGTGG<br>ATAACGCCCTCCAATCGGGTAACTCCCAGG<br>AGAGTGTCACAGAGCAGGACAGCAAGGACA<br>GCACCTACAGCCTCAGCAGCACCCTGACGC<br>TGAGCAAAGCAGACTACGAGAAACACAAAG<br>TCTACGCCTGCGAAGTCACCCATCAGGGCC<br>TGAGCTCGCCCGTCACAAAGAGCTTCAACA<br>GGGGAGAGTGTTAG |

CJM112

| SEQ ID NO: 24 (Kabat) | HCDR1 | SYWMS |
| --- | --- | --- |
| SEQ ID NO: 26 (Kabat) | HCDR2 | NIKQDGSEKYYVDSVKG |
| SEQ ID NO: 28 (Kabat) | HCDR3 | DRGSLYY |
| SEQ ID NO: 25 (Chothia) | HCDR1 | GFTFSSY |
| SEQ ID NO: 27 (Chothia) | HCDR2 | KQDGSE |
| SEQ ID NO: 29 (Chothia) | HCDR3 | DRGSLYY |
| SEQ ID NO: 30 | VH | EVQLVESGGDLVQPGGSLRLSCAASGFTFSS<br>YWMSVWRQAPGKGLEWVANIKQDGSEKYYV<br>DSVKGRFTISRDNAKNSLYLQMNSLRAEDTAV<br>YYCARDRGSLYYWGQGTLVTVSS |
| SEQ ID NO: 34 | DNA VH | GAGGTGCAGCTGGTCGAGTCTGGCGGCGA<br>CCTGGTGCAGCCTGGCGGCAGCCTGAGAC<br>TGAGCTGCGCCGCCAGCGGCTTCACCTTCA<br>GCAGCTACTGGATGTCCTGGGTCCGCCAGG<br>CCCCTGGCAAAGGCCTCGAATGGGTGGCCA<br>ACATCAAGCAGGACGGCAGCGAGAAGTACT<br>ACGTGGACAGCGTGAAGGGCCGGTTCACCA<br>TCAGCCGGGACAACGCCAAGAACAGCCTGT<br>ACCTGCAGATGAACAGCCTGCGGGCCGAG<br>GACACCGCCGTGTACTACTGCGCCAGGGAC<br>CGGGGCAGCCTGTACTATTGGGGCCAGGG<br>CACCCTGGTCACCGTGTCCAGC |

TABLE 4-continued

Sequences according to embodiments of the invention

| SEQ ID NUMBER | Ab region | Sequence |
| --- | --- | --- |
| SEQ ID NO: 31 | Heavy Chain | EVQLVESGGDLVQPGGSLRLSCAASGFTFSSYWMSVWRQAPGKGLEWVANIKQDGSEKYYVDSVKGRFTISRDNAKNSLYLQMNSLRAEDTAVYYCARDRGSLYYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| SEQ ID NO: 35 | DNA Heavy Chain | GAGGTGCAGCTGGTCGAGTCTGGCGGCGACCTGGTGCAGCCTGGCGGCAGCCTGAGACTGAGCTGCGCCGCCAGCGGCTTCACCTTCAGCAGCTACTGGATGTCCTGGGTCCGCCAGGCCCCTGGCAAAGGCCTCGAATGGGTGGCCAACATCAAGCAGGACGGCAGCGAGAAGTACTACGTGGACAGCGTGAAGGGCCGGTTCACCATCAGCCGGGACAACGCCAAGAACAGCCTGTACCTGCAGATGAACAGCCTGCGGGCCGAGGACACCGCCGTGTACTACTGCGCCAGGGACCGGGGCAGCCTGTACTATTGGGGCCAGGGCACCCTGGTCACCGTGTCCAGCGCTAGCACCAAGGGCCCCAGCGTGTTCCCCCTGGCCCCCAGCAGCAAGAGCACCAGCGGCGGCACAGCCGCCCTGGGCTGCCTGGTGAAGGACTACTTCCCCGAGCCCGTGACCGTGTCCTGGAACAGCGGAGCCCTGACCTCCGGCGTGCACACCTTCCCCGCCGTGCTGCAGAGCAGCGGCCTGTACAGCCTGTCCAGCGTGGTGACAGTGCCCAGCAGCAGCCTGGGCACCCAGACCTACATCTGCAACGTGAACCACAAGCCCAGCAACACCAAGGTGGACAAGAGAGTGGAGCCCAAGAGCTGCGACAAGACCCACACCTGCCCCCCCTGCCCAGCCCCAGAGCTGCTGGGCGGACCCTCCGTGTTCCTGTTCCCCCCCAAGCCCAAGGACACCCTGATGATCAGCAGGACCCCCGAGGTGACCTGCGTGGTGGTGGACGTGAGCCACGAGGACCCAGAGGTGAAGTTCAACTGGTACGTGGACGGCGTGGAGGTGCACAACGCCAAGACCAAGCCCAGAGAGGAGCAGTACAACAGCACCTACAGGGTGGTGTCCGTGCTGACCGTGCTGCACCAGGACTGGCTGAACGGCAAGGAATACAAGTGCAAGGTCTCCAACAAGGCCCTGCCAGCCCCCATCGAAAAGACCATCAGCAAGGCCAAGGGCCAGCCACGGGAGCCCCAGGTGTACACCCTGCCCCCCTCCCGGGAGGAGATGACCAAGAACCAGGTGTCCCTGACCTGTCTGGTGAAGGGCTTCTACCCCAGCGACATCGCCGTGGAGTGGGAGAGCAACGGCCAGCCCGAGAACAACTACAAGACCACCCCCCCAGTGCTGGACAGCGACGGCAGCTTCTTCCTGTACAGCAAGCTGACCGTGGACAAGTCCAGGTGGCAGCAGGGCAACGTGTTCAGCTGCAGCGTGATGCACGAGGCCCTGCACAACCACTACACCCAGAAGAGCCTGAGCCTGTCCCCCGGCAAG |
| SEQ ID NO: 16 (Kabat) | LCDR1 | RPSQGINWELA |
| SEQ ID NO: 18 (Kabat) | LCDR2 | DASSLEQ |
| SEQ ID NO: 20 (Kabat) | LCDR3 | QQFNSYPLT |
| SEQ ID NO: 17 (Chothia) | LCDR1 | SQGINWE |
| SEQ ID NO: 19 (Chothia) | LCDR2 | DAS |
| SEQ ID NO: 21 (Chothia) | LCDR3 | FNSYPL |

TABLE 4-continued

Sequences according to embodiments of the invention

| SEQ ID NUMBER | Ab region | Sequence |
| --- | --- | --- |
| SEQ ID NO: 22 | VL | AIQLTQSPSSLSASVGDRVTITCRPSQGINWEL AWYQQKPGKAPKLLIYDASSLEQGVPSRFSG SGSGTDFTLTISSLQPEDFATYYCQQFNSYPL TFGGGTKVEIK |
| SEQ ID NO: 36 | DNA VL | GCCATCCAGCTGACCCAGAGCCCCAGCAGC CTGAGCGCCAGCGTGGGCGACAGAGTGAC CATCACCTGTCGGCCCAGCCAGGGCATCAA CTGGGAGCTGGCCTGGTATCAGCAGAAGCC TGGCAAGGCCCCCAAGCTGCTGATCTACGA CGCCAGCTCCCTGGAACAGGGCGTGCCCA GCCGGTTCAGCGGCAGCGGATCCGGCACC GACTTCACCCTGACCATCAGCTCCCTGCAG CCCGAGGACTTCGCCACCTACTACTGCCAG CAGTTCAACAGCTACCCCCTGACCTTCGGC GGAGGCACCAAGGTGGAAATCAAG |
| SEQ ID NO: 23 | Light Chain | AIQLTQSPSSLSASVGDRVTITCRPSQGINWEL AWYQQKPGKAPKLLIYDASSLEQGVPSRFSG SGSGTDFTLTISSLQPEDFATYYCQQFNSYPL TFGGGTKVEIKRTVAAPSVFIFPPSDEQLKSGT ASVVCLLNNFYPREAKVQWKVDNALQSGNSQ ESVTEQDSKDSTYSLSSTLTLSKADYEKHKVY ACEVTHQGLSSPVTKSFNRGEC |
| SEQ ID NO: 37 | DNA Light Chain | GAGGTGCAGCTGGTCGAGTCTGGCGGCGA CCTGGTGCAGCCTGGCGGCAGCCTGAGAC TGAGCTGCGCCGCCAGCGGCTTCACCTTCA GCAGCTACTGGATGTCCTGGGTCCGCCAGG CCCCTGGCAAAGGCCTCGAATGGGTGGCCA ACATCAAGCAGGACGGCAGCGAGAAGTACT ACGTGGACAGCGTGAAGGGCCGGTTCACCA TCAGCCGGGACAACGCCAAGAACAGCCTGT ACCTGCAGATGAACAGCCTGCGGGCCGAG GACACCGCCGTGTACTACTGCGCCAGGGAC CGGGGCAGCCTGTACTATTGGGGCCAGGG CACCCTGGTCACCGTGTCCAGCGCTAGCAC CAAGGGCCCCAGCGTGTTCCCCCTGGCCC CCAGCAGCAAGAGCACCAGCGGCGGCACA GCCGCCCTGGGCTGCCTGGTGAAGGACTA CTTCCCCGAGCCCGTGACCGTGTCCTGGAA CAGCGGAGCCCTGACCTCCGGCGTGCACA CCTTCCCCGCCGTGCTGCAGAGCAGCGGC CTGTACAGCCTGTCCAGCGTGGTGACAGTG CCCAGCAGCAGCCTGGGCACCCAGACCTAC ATCTGCAACGTGAACCACAAGCCCAGCAAC ACCAAGGTGGACAAGAGAGTGGAGCCCAAG AGCTGCGACAAGACCCACACCTGCCCCCCC TGCCCAGCCCCAGAGCTGCTGGGCGGACC CTCCGTGTTCCTGTTCCCCCCCAAGCCCAA GGACACCCTGATGATCAGCAGGACCCCCGA GGTGACCTGCGTGGTGGTGGACGTGAGCC ACGAGGACCCAGAGGTGAAGTTCAACTGGT ACGTGGACGGCGTGGAGGTGCACAACGCC AAGACCAAGCCCAGAGAGGAGCAGTACAAC AGCACCTACAGGGTGGTGTCCGTGCTGACC GTGCTGCACCAGGACTGGCTGAACGGCAAG GAATACAAGTGCAAGGTCTCCAACAAGGCC CTGCCAGCCCCCATCGAAAAGACCATCAGC AAGGCCAAGGGCCAGCCACGGGAGCCCCA GGTGTACACCCTGCCCCCCTCCCGGGAGG AGATGACCAAGAACCAGGTGTCCCTGACCT GTCTGGTGAAGGGCTTCTACCCCAGCGACA TCGCCGTGGAGTGGGAGAGCAACGGCCAG CCCGAGAACAACTACAAGACCACCCCCCCA GTGCTGGACAGCGACGGCAGCTTCTTCCTG TACAGCAAGCTGACCGTGGACAAGTCCAGG TGGCAGCAGGGCAACGTGTTCAGCTGCAGC GTGATGCACGAGGCCCTGCACAACCACTAC ACCCAGAAGAGCCTGAGCCTGTCCCCCGGC AAG |

Throughout the text of this application, should there be a discrepancy between the text of the specification (e.g., Table 4) and the sequence listing, the text of the specification shall prevail.

The invention claimed is:

1. A method of selectively treating a patient having asthma with a neutralizing IL-17A antibody or antigen-binding portion thereof, comprising:
   a) selecting the patient for treatment with the IL-17A antibody or antigen-binding portion thereof on the basis of the patient having a total serum concentration of IgE below a threshold of 150 international units per milliliter (IU/mL); and
   b) thereafter, administering a therapeutically effective amount of the IL-17A antibody or antigen-binding portion thereof to the patient.

2. The method according to claim 1, wherein step a) additionally comprises selecting the patient for treatment with the IL-17A antibody or antigen-binding portion thereof on the basis of the patient also having an eosinophil count in peripheral blood below 300 per μL.

3. The method according to claim 1, wherein the patient has moderate to severe asthma.

4. A method of selectively treating a patient having asthma, comprising:
   a) assaying a biological sample from the patient for a total serum concentration of IgE; and
   b) thereafter, selectively administering to the patient either:
      i. a therapeutically effective amount of a neutralizing IL-17A antibody or antigen-binding portion thereof on the basis of the biological sample from the patient having a total serum concentration of IgE below a threshold of 150 IU/mL; or
      ii. a therapeutically effective amount of an asthma agent other than an IL-17A antibody or antigen-binding portion thereof on the basis of the biological sample from the patient having a total serum concentration of IgE of a threshold of 150 IU/mL or more.

5. The method according to claim 4, wherein the step of assaying comprises assaying the biological sample using an immunoassay.

6. The method according to claim 5, wherein the step of assaying comprises a total IgE test.

7. A method of selectively treating a patient having asthma with a neutralizing IL-17A antibody or antigen-binding portion thereof, comprising:
   a) assaying a biological sample from the patient for a total serum concentration of IgE;
   b) thereafter, selecting the patient for treatment with the IL-17A antibody or antigen-binding portion thereof on the basis of the biological sample from the patient having a total serum concentration of IgE below a threshold of 150 IU/mL; and
   c) thereafter, administering a therapeutically effective amount of the IL-17A antibody or antigen-binding portion thereof to the patient.

8. The method according to claim 7, wherein step a) additionally comprises assaying a biological sample from the patient for eosinophil count in peripheral blood, and administering the IL-17A antibody or antigen-binding portion thereof to the patient on the basis of the biological sample from the patient having a total serum concentration of IgE below a threshold of 150 IU/mL and also an eosinophil count in peripheral blood below 300 per μL.

9. The method according to claim 7, wherein the biological sample is selected from the group consisting of blood, serum, or plasma, preferably serum.

10. A method of selectively treating an asthma patient, comprising administering to the patient a neutralizing IL-17A antibody or antigen-binding portion thereof on the basis of the patient having been previously determined to have a total serum concentration of IgE below a threshold of 150 IU/mL.

11. The method according to claim 10, wherein the IL-17 antibody or antigen-binding portion thereof is a human IL-17 antibody comprising:
   a) an immunoglobulin $V_H$ domain comprising the amino acid sequence set forth as SEQ ID NO:30 and an immunoglobulin $V_L$ domain comprising the amino acid sequence set forth as SEQ ID NO:22;
   b) an immunoglobulin $V_H$ domain comprising the hypervariable regions set forth as SEQ ID NO:24, SEQ ID NO:26, and SEQ ID NO:28 and an immunoglobulin $V_L$ domain comprising the hypervariable regions set forth as SEQ ID NO:16, SEQ ID NO:18 and SEQ ID NO:20; or
   c) an immunoglobulin $V_H$ domain comprising the hypervariable regions set forth as SEQ ID NO:25, SEQ ID NO:27 and SEQ ID NO:29 and an immunoglobulin $V_L$ domain comprising the hypervariable regions set forth as SEQ ID NO:17, SEQ ID NO:19 and SEQ ID NO:21.

12. The method according to claim 11, wherein the human IL-17 antibody comprises the light chain set forth as SEQ ID NO:23 and the heavy chain set forth as SEQ ID NO:31.

13. The method according to claim 10, wherein the IL-17 antibody or antigen-binding portion thereof is a human IL-17 antibody comprising:
   a) an immunoglobulin $V_H$ domain comprising the amino acid sequence set forth as SEQ ID NO:8 and an immunoglobulin $V_L$ domain comprising the amino acid sequence set forth as SEQ ID NO:10;
   b) an immunoglobulin $V_H$ domain comprising the hypervariable regions set forth as SEQ ID NO:1, SEQ ID NO:2, and SEQ ID NO:3 and an immunoglobulin $V_L$ domain comprising the hypervariable regions set forth as SEQ ID NO:4, SEQ ID NO:5 and SEQ ID NO:6; or
   c) an immunoglobulin $V_H$ domain comprising the hypervariable regions set forth as SEQ ID NO:11, SEQ ID NO:12 and SEQ ID NO:13 and an immunoglobulin $V_L$ domain comprising the hypervariable regions set forth as SEQ ID NO:4, SEQ ID NO:5 and SEQ ID NO:6.

14. The method according to claim 13, wherein the human IL-17 antibody comprises the light chain set forth as SEQ ID NO:14 and the heavy chain set forth as SEQ ID NO:15.

15. The method according to claim 10, wherein the IL-17 antibody IL-17A antibody or antigen-binding portion thereof is secukinumab or CJM112, wherein the CJM12 antibody comprises the light chain set forth as SEQ ID NO:23 and the heavy chain set forth as SEQ ID NO:31.

* * * * *

```
                       SEQUENCE LISTING

<160> NUMBER OF SEQ ID NOS: 37

<210> SEQ ID NO 1
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Asn Tyr Trp Met Asn
1               5

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ala Ile Asn Gln Asp Gly Ser Glu Lys Tyr Tyr Val Gly Ser Val Lys
1               5                   10                  15

Gly

<210> SEQ ID NO 3
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Asp Tyr Tyr Asp Ile Leu Thr Asp Tyr Tyr Ile His Tyr Trp Tyr Phe
1               5                   10                  15

Asp Leu

<210> SEQ ID NO 4
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Arg Ala Ser Gln Ser Val Ser Ser Ser Tyr Leu Ala
1               5                   10

<210> SEQ ID NO 5
<211> LENGTH: 7
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 5

Gly Ala Ser Ser Arg Ala Thr
1               5

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gln Gln Tyr Gly Ser Ser Pro Cys Thr
1               5

<210> SEQ ID NO 7
<211> LENGTH: 381
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7
gaggtgcagt tggtggagtc tgggggaggc ttggtccagc ctggggggtc cctgagactc      60
tcctgtgcag cctctggatt cacctttagt aactattgga tgaactgggt ccgccaggct     120
ccagggaaag gctggagtg gtggccgcc ataaaccaag atggaagtga aaatactat        180 gtgggctctg tgaagggccg attcaccatc tccagagaca cgccaagaa ctcactgtat     240 ctgcaaatga acagcctgag agtcgaggac acggctgtgt attactgtgt gagggactat    300
tacgatattt tgaccgatta ttacatccac tattggtact cgatctctg gggccgtggc    360 accctggtca ctgtctcctc a                                               381

<210> SEQ ID NO 8
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95
```

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 9
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 9
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccgtg caccttcggc     300
caagggacac gactggagat taaacga                                          327

<210> SEQ ID NO 10
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Thr Phe Gly Gln Gly Thr Arg Leu Glu Ile Lys Arg
            100                 105

<210> SEQ ID NO 11
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 11

Gly Phe Thr Phe Ser Asn Tyr Trp Met Asn
1               5                   10

```
<210> SEQ ID NO 12
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ala Ile Asn Gln Asp Gly Ser Glu Lys Tyr Tyr
1               5                   10

<210> SEQ ID NO 13
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Cys Val Arg Asp Tyr Tyr Asp Ile Leu Thr Asp Tyr Tyr Ile His Tyr
1               5                   10                  15

Trp Tyr Phe Asp Leu Trp Gly
            20

<210> SEQ ID NO 14
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190
```

```
Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 15
<211> LENGTH: 240
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

<210> SEQ ID NO 16
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Arg Pro Ser Gln Gly Ile Asn Trp Glu Leu Ala
1               5                   10
```

```
<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ser Gln Gly Ile Asn Trp Glu
1               5

<210> SEQ ID NO 18
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Asp Ala Ser Ser Leu Glu Gln
1               5

<210> SEQ ID NO 19
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Asp Ala Ser
1

<210> SEQ ID NO 20
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gln Gln Phe Asn Ser Tyr Pro Leu Thr
1               5

<210> SEQ ID NO 21
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Phe Asn Ser Tyr Pro Leu
1               5

<210> SEQ ID NO 22
<211> LENGTH: 107
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Ala Ile Gln Leu Thr Gln Ser Pro Ser Ser Leu Ser Ala Ser Val Gly
1               5                   10                  15

Asp Arg Val Thr Ile Thr Cys Arg Pro Ser Gln Gly Ile Asn Trp Glu
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Gln Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 23
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Ala Ile Gln Leu Thr Gln Ser Pro Ser Ser Leu Ser Ala Ser Val Gly
1               5                   10                  15

Asp Arg Val Thr Ile Thr Cys Arg Pro Ser Gln Gly Ile Asn Trp Glu
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Gln Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 24
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Ser Tyr Trp Met Ser
1               5

<210> SEQ ID NO 25
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Gly Phe Thr Phe Ser Ser Tyr
1               5

<210> SEQ ID NO 26
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Asn Ile Lys Gln Asp Gly Ser Glu Lys Tyr Tyr Val Asp Ser Val Lys
1               5                   10                  15

Gly

<210> SEQ ID NO 27
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Lys Gln Asp Gly Ser Glu
1               5

<210> SEQ ID NO 28
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Asp Arg Gly Ser Leu Tyr Tyr

```
<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Asp Arg Gly Ser Leu Tyr Tyr
1               5

<210> SEQ ID NO 30
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ser Leu Tyr Tyr Trp Gly Gln Gly Thr Leu Val
            100                 105                 110

Thr Val Ser Ser
        115

<210> SEQ ID NO 31
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                 85                  90                  95

Ala Arg Asp Arg Gly Ser Leu Tyr Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 32
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 32

```
gaggtgcagt tggtggagtc tgggggaggc ttggtccagc ctggggggtc cctgagactc    60
tcctgtgcag cctctggatt cacctttagt aactattgga tgaactgggt ccgccaggct   120
ccagggaaag gctggagtg gtggccgcc ataaaccaag atggaagtga aaatactat   180
gtgggctctg tgaagggccg attcaccatc tccagagaca acgccaagaa ctcactgtat   240
ctgcaaatga acagcctgag agtcgaggac acggctgtgt attactgtgt gagggactat   300
tacgatattt tgaccgatta ttacatccac tattggtact cgatctctg ggccgtggc   360
accctggtca ctgtctcctc agcctccacc aagggcccat cggtcttccc cctggcaccc   420
tcctccaaga gcacctctgg gggcacagcg gccctgggct gcctggtcaa ggactacttc   480
cccgaaccgg tgacggtgtc gtggaactca ggcgccctga ccagcggcgt gcacaccttc   540
ccggctgtcc tacagtcctc aggactctac tccctcagca gcgtggtgac cgtgccctcc   600
agcagcttgg gcacccagac ctacatctgc aacgtgaatc acaagcccag caacaccaag   660
gtggacaaga gagttgagcc caaatcttgt gacaaaactc acacatgccc accgtgccca   720
taa                                                                  723
```

<210> SEQ ID NO 33
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 33

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccgtg cacccttcggc   300
caagggacac gactggagat taaacgaact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagacta cgagaaacac aaagtctacg cctgcgaagt cacccatcag   600
ggcctgagct cgcccgtcac aaagagcttc aacaggggag agtgttag                  648
```

<210> SEQ ID NO 34
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 34

```
gaggtgcagc tggtcgagtc tggcggcgac ctggtgcagc tggcggcag cctgagactg    60
agctgcgccg ccagcggctt caccttcagc agctactgga tgtcctgggt ccgccaggcc   120
```

| | |
|---|---|
| cctggcaaag gcctcgaatg ggtggccaac atcaagcagg acggcagcga gaagtactac | 180 |
| gtggacagcg tgaagggccg gttcaccatc agccgggaca acgccaagaa cagcctgtac | 240 |
| ctgcagatga acagcctgcg ggccgaggac accgccgtgt actactgcgc cagggaccgg | 300 |
| ggcagcctgt actattgggg ccagggcacc ctggtcaccg tgtccagc | 348 |

<210> SEQ ID NO 35
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 35

| | |
|---|---|
| gaggtgcagc tggtcgagtc tggcggcgac ctggtgcagc tggcggcag cctgagactg | 60 |
| agctgcgccg ccagcggctt caccttcagc agctactgga tgtcctgggt ccgccaggcc | 120 |
| cctggcaaag gcctcgaatg ggtggccaac atcaagcagg acggcagcga gaagtactac | 180 |
| gtggacagcg tgaagggccg gttcaccatc agccgggaca acgccaagaa cagcctgtac | 240 |
| ctgcagatga acagcctgcg ggccgaggac accgccgtgt actactgcgc cagggaccgg | 300 |
| ggcagcctgt actattgggg ccagggcacc ctggtcaccg tgtccagcgc tagcaccaag | 360 |
| ggccccagcg tgttccccct ggcccccagc agcaagagca ccagcggcgg cacagccgcc | 420 |
| ctgggctgcc tggtgaagga ctacttcccc gagcccgtga ccgtgtcctg aacagcgga | 480 |
| gccctgacct ccggcgtgca caccttcccc gccgtgctgc agagcagcgg cctgtacagc | 540 |
| ctgtccagcg tggtgacagt gcccagcagc agcctgggca cccagaccta catctgcaac | 600 |
| gtgaaccaca gcccagcaa caccaaggtg gacaagagag tggagcccaa gagctgcgac | 660 |
| aagacccaca cctgcccccc ctgcccagcc ccagagctgc tgggcggacc ctccgtgttc | 720 |
| ctgttccccc ccaagcccaa ggacaccctg atgatcagca ggaccccga ggtgacctgc | 780 |
| gtggtggtgg acgtgagcca cgaggaccca gaggtgaagt tcaactggta cgtggacggc | 840 |
| gtggaggtgc acaacgccaa gaccaagccc agagaggagc agtacaacag cacctacagg | 900 |
| gtggtgtccg tgctgaccgt gctgcaccag gactggctga acggcaagga atacaagtgc | 960 |
| aaggtctcca acaaggccct gccagccccc atcgaaaaga ccatcagcaa ggccaagggc | 1020 |
| cagccacggg agcccaggt gtacaccctg ccccctccc gggaggagat gaccaagaac | 1080 |
| caggtgtccc tgacctgtct ggtgaagggc ttctacccca gcgacatcgc cgtggagtgg | 1140 |
| gagagcaacg gccagcccga gaacaactac aagaccaccc cccagtgct ggacagcgac | 1200 |
| ggcagcttct cctgtacag caagctgacc gtggacaagt ccaggtggca gcagggcaac | 1260 |
| gtgttcagct gcagcgtgat gcacgaggcc ctgcacaacc actacaccca gaagagcctg | 1320 |
| agcctgtccc ccggcaag | 1338 |

<210> SEQ ID NO 36
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 36

| | |
|---|---|
| gccatccagc tgacccagag ccccagcagc ctgagcgcca gcgtgggcga cagagtgacc | 60 |

```
atcacctgtc ggcccagcca gggcatcaac tgggagctgg cctggtatca gcagaagcct    120
ggcaaggccc ccaagctgct gatctacgac gccagctccc tggaacaggg cgtgcccagc    180
cggttcagcg gcagcggatc cggcaccgac ttcaccctga ccatcagctc cctgcagccc    240
gaggacttcg ccacctacta ctgccagcag ttcaacagct accccctgac cttcggcgga    300
ggcaccaagg tggaaatcaa g                                              321
```

<210> SEQ ID NO 37
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 37

```
gaggtgcagc tggtcgagtc tggcggcgac ctggtgcagc ctggcggcag cctgagactg     60
agctgcgccg ccagcggctt caccttcagc agctactgga tgtcctgggt ccgccaggcc    120
cctggcaaag gcctcgaatg ggtggccaac atcaagcagg acggcagcga aagtactac     180 gtggacagcg tgaagggccg gttcaccatc agccgggaca cgccaagaa cagcctgtac    240 ctgcagatga acagcctgcg ggccgaggac accgccgtgt actactgcgc cagggaccgg    300
ggcagcctgt actattgggg ccagggcacc ctggtcaccg tgtccagcgc tagcaccaag    360
ggccccagcg tgttcccccct ggcccccagc agcaagagca ccagcggcgg cacagccgcc    420
ctgggctgcc tggtgaagga ctacttcccc gagcccgtga ccgtgtcctg aacagcgga    480 gccctgacct ccggcgtgca caccttcccc gccgtgctgc agagcagcgg cctgtacagc    540
ctgtccagcg tggtgacagt gccacagcag agcctgggca cccagaccta catctgcaac    600
gtgaaccaca gcccagcaa caccaaggtg gacaagagag tggagcccaa gagctgcgac    660
aagacccaca cctgcccccc ctgcccagcc cagagctgc tgggcggacc ctccgtgttc    720
ctgttccccc ccaagcccaa ggacaccctg atgatcagca ggaccccga ggtgacctgc    780 gtggtggtgg acgtgagcca cgaggaccca gaggtgaagt tcaactggta cgtggacggc    840
gtggaggtgc acaacgccaa gaccaagccc agagaggagc agtacaacag cacctacagg    900
gtggtgtccg tgctgaccgt gctgcaccag gactggctga acggcaagga atacaagtgc    960
aaggtctcca acaaggccct gccagccccc atcgaaaaga ccatcagcaa ggccaagggc    1020
cagccacggg agcccaggt gtacaccctg cccccctccc ggaggagat gaccaagaac    1080 caggtgtccc tgacctgtct ggtgaaggc ttctacccca gcgacatcgc cgtggagtgg    1140
gagagcaacg gccagcccga gaacaactac aagaccaccc ccccagtgct ggacagcgac    1200
ggcagcttct tcctgtacag caagctgacc gtggacaagt ccaggtggca gcagggcaac    1260
gtgttcagct gcagcgtgat gcacgaggcc ctgcacaacc actacaccca gaagagcctg    1320
agcctgtccc ccggcaag                                                 1338
```